(12) United States Patent
Kinoshita

(10) Patent No.: US 8,765,417 B2
(45) Date of Patent: Jul. 1, 2014

(54) METHOD OF ELONGATING DNA THROUGH IMMOBILIZING PRIMER DNA CHAINS ON A SUBSTRATE, A METHOD OF AMPLIFYING A DNA CHAIN

(75) Inventor: Kenji Kinoshita, Hyogo (JP)

(73) Assignees: Sumitomo Bakelite Co., Ltd., Tokyo (JP); DNA Chip Research Inc., Kyogo (JP)

( * ) Notice: Subject to any disclaimer, the term of this patent is extended or adjusted under 35 U.S.C. 154(b) by 1048 days.

(21) Appl. No.: 11/792,512

(22) PCT Filed: Nov. 29, 2005

(86) PCT No.: PCT/JP2005/021922
§ 371 (c)(1),
(2), (4) Date: Jun. 7, 2007

(87) PCT Pub. No.: WO2006/062009
PCT Pub. Date: Jun. 15, 2006

(65) Prior Publication Data
US 2008/0032348 A1    Feb. 7, 2008

(30) Foreign Application Priority Data

Dec. 9, 2004   (JP) .................. 2004-357224
Jun. 23, 2005  (JP) .................. 2005-184136

(51) Int. Cl.
| | |
|---|---|
| *C12Q 1/68* | (2006.01) |
| *C12P 19/34* | (2006.01) |
| *C07H 21/02* | (2006.01) |
| *C07H 21/04* | (2006.01) |

(52) U.S. Cl.
USPC ........ 435/91.2; 435/6.12; 536/23.1; 536/24.3

(58) Field of Classification Search
USPC ................ 435/6.1, 6.12, 91.2; 536/23.1, 24.3
See application file for complete search history.

(56) References Cited

U.S. PATENT DOCUMENTS

| | | | | |
|---|---|---|---|---|
| 5,484,701 A | * | 1/1996 | Cocuzza et al. | ............. 435/6.11 |
| 5,564,104 A | * | 10/1996 | Pourfarzaneh | .................. 588/20 |
| 2002/0086322 A1 | * | 7/2002 | Yu et al. | .............. 435/6 |
| 2005/0079506 A1 | * | 4/2005 | Leon et al. | ......... 435/6 |
| 2005/0176003 A1 | * | 8/2005 | Yokoyama et al. | ............. 435/6 |
| 2006/0067908 A1 | * | 3/2006 | Ding | ........................ 424/78.27 |

FOREIGN PATENT DOCUMENTS

| | | | |
|---|---|---|---|
| EP | 0 937 097 B1 | * | 8/2001 |
| JP | 2004-97173 | | 4/2004 |
| JP | 2004-198402 | | 7/2004 |
| WO | WO 03-046562 A1 | * | 5/2003 .......... G01N 33/53 |
| WO | 2005/029095 | | 3/2005 |

OTHER PUBLICATIONS

Trau et al., Genotyping on a Complementary Metal Oxide Semiconductor Silicon Polymerase Chain Reaction Chip with Integrated DNA Microarray, Anal. Chem. 2002, 74, 3168-3173.*

Pastinen et al., A System for Specific, High-throughput Genotyping by Allele-specific Primer Extension on Microarrays, Genome Res. 2000 10: 1031-1042.*

Carninci et al., Thermostabilization and thermoactivation of thermolabile enzymes by trehalose and its application for the synthesis of full length cDNA, Proc. Natl. Acad. Sci. USA, vol. 95, pp. 520-524, Jan. 1998. Biochemistry.*

Lewis et al., Phosphorylcholine-based polymers and their use in the prevention of biofouling, Colloids and Surfaces B: Biointerfaces, 18 (2000) 261-275.*

Takei et al., Regulation of Enzyme-Substrate Complexation by a Substrate Conjugated with a Phospholipid Polymer, Biomacromolecules 2004, 5, 858-862, Published on Web Mar. 10, 2004.*

Supplementary European Search Report for Application No. EP 05 81 1695 issued Mar. 6, 2009.

Sakai-Kato, et al., "An enzyme-immobilization method for integration of biofunctions on a microchip using a water-soluble amphiphilic phospholipid polymer having a reacting group", Lab on a Chip, vol. 4, No. 1, Feb. 2004, XP002515571, ISSN: 1473-0197.

Park et al., "Evaluation of 2-Methacryloyloxyethyl Phosphorylcholine Polymeric Nanoparticle for Immunoassay of C-Reactive Protein Detection", Analytical Chemistry, American Chemical Society, Columbus, US, vol. 76, No. 9, May 1, 2004, pp. 2649-2655, XP001196758, ISSN: 0003-2700.

Ishihara et al., "Why do phospholipid polymers reduce protein adsorption?", Journal of Biochemical materials Research, Wiley, New York, NY, US, vol. 39, No. 2, Jan. 1, 1998, pp. 323-330, XP002972153, ISSN: 0021-9304.

Kinoshita et al., "Multiple primer extension by DNA polymerase on a novel plastic DNA array coated with a biocompatible polymer", Nucleic Acids Research, 2007, vol. 35, No. 1, e3, XP002515573, ISSN: 1362-4962.

Imai et al., "A novel SNP detection technique utilizing a multiple primer extension (MPEX) on a phospholipid polymer-coated surface", Molecular Biosystems Aug. 2007, vol. 3, No. 8, Aug. 2007, pp. 547-553, XP002515574, ISSN: 1742-206X.

Adessi, Celine et al., "Solid phase DNA amplification: Characterization of primer attachment and amplification mechanisms", Nuclecic Acids Research, 200, vol. 28, No. 20, e87.

Fixe, F. et al., "Functionalization of poly(methyl methacrylate) (PMMA) as a substrate for DNA microarrays", Nucleic Acids Research, 2004, vol. 32, No. 1, e9.

Chromatography, Journal of Separation and Detection Sciences, Oct. 2004, vol. 25, No. Supplement 2, pp. 85-86.

Konno, T. et al., "Conjugation of Enzymes on Polymer Nanoparticles Covered with Phosphorylcholine Groups", Biomacromolecules, Apr. 2004, vol. 5, No. 2, pp. 342-347.

U.S. Appl. No. 10/572,332, filed Mar. 17, 2006, Applicant states this is copending.

U.S. Appl. No. 11/920,559, filed May 16, 2006, Copending, shared inventor.

* cited by examiner

*Primary Examiner* — Ardin Marschel
(74) *Attorney, Agent, or Firm* — Smith, Gambrell & Russell, LLP

(57) ABSTRACT

Primers for DNA elongation are immobilized onto a substrate having on the surface thereof a polymer substance which contains a first unit having a group derived from a phosphoester composing the hydrophilic section of a phospholipid, and a second unit having an activated ester group, and DNA elongation reaction is allowed to proceed in a reaction system having introduced therein a sample which contains DNA fragments having desired sequences and nucleotide monomers, by heating the reaction system up to a temperature causing thermal unfolding of the DNA chains, and then by cooling the reaction system down to a temperature for annealing.

22 Claims, 10 Drawing Sheets

```
                        SEQUENCE LISTING

<160> NUMBER OF SEQ ID NOS: 15

<210> SEQ ID NO 1
<211> LENGTH: 50
<212> TYPE: DNA
<213> ORGANISM: Escherichia coli

<400> SEQUENCE: 1
aaggcgggag ggagcgcaat ccgggagttt acaaatggac aaacttctat          50

<210> SEQ ID NO 2
<211> LENGTH: 16
<212> TYPE: DNA
<213> ORGANISM: Artificial Sequence
<220> FEATURE:
<223> OTHER INFORMATION: Designed DNA probe for SNP analysis for p53
      gene.
<220> FEATURE:
<221> NAME/KEY: misc_feature
<222> LOCATION: (16)..(16)
<223> OTHER INFORMATION: n stands for any base

<400> SEQUENCE: 2
atgggcggca tgaacn                                               16

<210> SEQ ID NO 3
<211> LENGTH: 16
<212> TYPE: DNA
<213> ORGANISM: Artificial Sequence
<220> FEATURE:
<223> OTHER INFORMATION: Designed DNA probe for SNP analysis for p53
      gene.
<220> FEATURE:
<221> NAME/KEY: misc_feature
<222> LOCATION: (16)..(16)
<223> OTHER INFORMATION: n stands for any base

<400> SEQUENCE: 3
tgaggatggg cctccn                                               16

<210> SEQ ID NO 4
<211> LENGTH: 19
<212> TYPE: DNA
<213> ORGANISM: Artificial Sequence
<220> FEATURE:
<223> OTHER INFORMATION: Designed DNA probe for SNP analysis for p53
      gene.
<220> FEATURE:
<221> NAME/KEY: misc_feature
<222> LOCATION: (19)..(19)
<223> OTHER INFORMATION: n stands for any base

<400> SEQUENCE: 4
ggaacagctt tgaggtgcn                                            19

<210> SEQ ID NO 5
<211> LENGTH: 19
<212> TYPE: DNA
<213> ORGANISM: Artificial Sequence
<220> FEATURE:
<223> OTHER INFORMATION: Designed DNA probe for SNP analysis for p53
      gene.
<220> FEATURE:
<221> NAME/KEY: misc_feature
<222> LOCATION: (19)..(19)
```

```
<223> OTHER INFORMATION: n stands for any base

<400> SEQUENCE: 5
ccaggacagg cacaaacan                                                19

<210> SEQ ID NO 6
<211> LENGTH: 18
<212> TYPE: DNA
<213> ORGANISM: Artificial Sequence
<220> FEATURE:
<223> OTHER INFORMATION: Designed DNA probe for SNP analysis for p53
      gene.

<400> SEQUENCE: 6
aaggcgggag ggagcgca                                                 18

<210> SEQ ID NO 7
<211> LENGTH: 18
<212> TYPE: DNA
<213> ORGANISM: Artificial Sequence
<220> FEATURE:
<223> OTHER INFORMATION: Designed DNA probe for SNP analysis for p53
      gene.

<400> SEQUENCE: 7
tgcgcucccu cccgccuu                                                 18

<210> SEQ ID NO 8
<211> LENGTH: 15
<212> TYPE: DNA
<213> ORGANISM: Artificial Sequence
<220> FEATURE:
<223> OTHER INFORMATION: Designed DNA probe for SNP analysis for p53
      gene.

<400> SEQUENCE: 8
accgtaaatg gatat                                                    15

<210> SEQ ID NO 9
<211> LENGTH: 21
<212> TYPE: DNA
<213> ORGANISM: Artificial Sequence
<220> FEATURE:
<223> OTHER INFORMATION: Designed DNA probe for SNP analysis for p53
      gene.

<400> SEQUENCE: 9
taaactcccg gattgcgctc c                                             21

<210> SEQ ID NO 10
<211> LENGTH: 21
<212> TYPE: DNA
<213> ORGANISM: Artificial Sequence
<220> FEATURE:
<223> OTHER INFORMATION: Designed DNA probe for SNP analysis for p53
      gene.

<400> SEQUENCE: 10
taaactcccg aattgcgctc c                                             21

<210> SEQ ID NO 11
<211> LENGTH: 21
<212> TYPE: DNA
<213> ORGANISM: Artificial Sequence
<220> FEATURE:
<223> OTHER INFORMATION: Designed DNA probe for SNP analysis for p53
      gene.
```

-continued

```
<400> SEQUENCE: 11
taaactcccg tattgcgctc c                                              21

<210> SEQ ID NO 12
<211> LENGTH: 21
<212> TYPE: DNA
<213> ORGANISM: Artificial Sequence
<220> FEATURE:
<223> OTHER INFORMATION: Designed DNA probe for SNP analysis for p53
      gene.

<400> SEQUENCE: 12
taaactcccg cattgcgctc c                                              21

<210> SEQ ID NO 13
<211> LENGTH: 21
<212> TYPE: DNA
<213> ORGANISM: Artificial Sequence
<220> FEATURE:
<223> OTHER INFORMATION: Designed DNA probe for SNP analysis for p53
      gene.

<400> SEQUENCE: 13
taaactcccg attgcgctcc c                                              21

<210> SEQ ID NO 14
<211> LENGTH: 31
<212> TYPE: DNA
<213> ORGANISM: Artificial Sequence
<220> FEATURE:
<223> OTHER INFORMATION: Designed DNA probe for SNP analysis for p53
      gene.

<400> SEQUENCE: 14
taaactcccg gattgcgctc ccucccgccu u                                   31

<210> SEQ ID NO 15
<211> LENGTH: 60
<212> TYPE: DNA
<213> ORGANISM: Artificial Sequence
<220> FEATURE:
<223> OTHER INFORMATION: Designed DNA probe for SNP analysis for p53
      gene.

<400> SEQUENCE: 15
ggtggataga agtttgtcca tttgtaaact cccggattgc gctccctccc gcctttctcc    60
```

METHOD OF ELONGATING DNA THROUGH IMMOBILIZING PRIMER DNA CHAINS ON A SUBSTRATE, A METHOD OF AMPLIFYING A DNA CHAIN

TECHNICAL FIELD

The present invention relates to a method of elongating DNA chains through immobilizing primer DNA chains onto the surface of a predetermined plastic substrate, a method of amplifying a DNA chain, and a microarray for DNA chain elongation used for these methods.

BACKGROUND ART

Non-Patent Document 1 discloses a technique of proceeding DNA amplification based on solid-phase PCR (Polymerase Chain Reaction), using a DNA microarray having DNA chains, which act as primers, bound through a covalent bond to the surface of a glass substrate modified with a predetermined amino-silane reagent.

Non-Patent Document 2 gives a description suggesting feasibility of a device applicable to the novel PCR technique, based on characteristics of hybridization with a predetermined DNA chain and thermal stability under PCR-like environment, evaluated using a DNA microarray having a poly (methyl methacrylate) in place of a glass substrate, and having DNA fragments immobilized on the surface thereof.

[Non-Patent Document 1] Adessi, Celine et al., "Solid phase DNA amplification: Characterization of primer attachment and amplification mechanisms", Nucleic Acids Research, 2000, Vol. 20, No. 20, e87

[Non-Patent Document 2] Fixe, F. et al., "Functionalization of poly(methyl methacrylate) (PMMA) as a substrate for DNA microarrays", Nucleic Acids Research, 2004, Jan. 12, Vol. 32, No. 1, e9

DISCLOSURE OF THE INVENTION

The present inventors tried the DNA chain elongation reaction based on the MPEC (Multiple Primer Extension on a Chip) process, using various DNA microarrays represented by those described in Non-Patent Documents 1, 2 and so forth, and found out a phenomenon that the thermal unfolding after the DNA chains are elongated, or annealed, using the template DNA chains bound to the primers results in dropping of the primers, once immobilized to the DNA microarray substrate, together with the template DNA, and then solved this problem by using a substrate having a predetermined polymer substance provided to the surface thereof, and thereby completed the present invention.

According to the present invention, there is provided a method of elongating DNA chains, which includes immobilizing primers for DNA elongation onto a substrate having on the surface thereof a polymer substance which contains a first unit having a group derived from a phosphoester composing the hydrophilic section of a phospholipid, and a second unit having a carboxylic acid-derived group configured by an electron-attractive substitutive group bound to a carbonyl group, heating a reaction system having introduced therein a sample containing template DNA fragments or template RNA fragments having desired sequences, an enzyme system for DNA chain elongation and nucleotide monomers, up to a temperature causing thermal unfolding of the DNA chains (referred to as "thermal unfolding temperature", hereinafter);

cooling the reaction system down to a temperature for annealing (referred to as "annealing temperature", hereinafter); and allowing elongation reaction of the DNA chains to proceed in the reaction system, wherein all of these processes are allowed to proceed in the same liquid phase system.

By immobilizing the primers to a predetermined substrate, by annealing the primers with the template DNA fragments, or by hybridizing the template RNA fragments, so as to proceed DNA chain elongation reaction in this way, and by allowing thermal unfolding to proceed after the reaction, the template DNA fragments or template RNA fragments can be released from DNA forming double strands on the substrate, while keeping the single-strand DNA elongated from the primers remained on the substrate.

Although it has conventionally been necessary for a washing process to remove the DNA fragments or RNA fragments which have not been incorporated into the double strand, there are no DNA fragments nor RNA fragments non-specifically adsorption to the substrate, and this is supposedly contributive to effectively proceed enzymatic reaction involved in the DNA chain elongation, making it no more necessary to wash the substrate before the elongation reaction.

Although the conventional procedure, involving the individual processes of hybridization, washing, and elongation under addition of enzyme and monomers, was such as allowing the hybridization and the elongation reaction to proceed in separate liquid phases, the present invention makes it possible to proceed the hybridization and the elongation reaction in the same liquid phase.

In this method of elongating DNA chains, the group derived from phosphoester contained in the first unit of the substrate may be any one of phosphoryl choline group, phosphoryl ethanolamine group, phosphoryl serine group, phosphoryl inositol group, phosphoryl glycerol group, and phosphatidyl phosphoryl glycerol group.

By providing an environment similar to phospholipid onto the surface of the substrate in this way, the DNA chain elongation reaction can now proceed in an environment similar to the intracellular one. The DNA chain elongation can therefore be proceeded under more milder conditions.

In the above-described method of elongating DNA chains, each of the primers may be a DNA fragment in which one base of a base sequence containing a characteristic sequence of a predetermined target gene is replaced with another base.

By this configuration, the method of elongating DNA chains of the present invention becomes applicable to analysis of single nucleotide polymorphisms (SNP).

In the above-described method of elongating DNA chains, each of the primers is composed of a predetermined number of base sequences, and is a DNA fragment having its own sequence out of complete sets.

By this configuration, the DNA chain elongation reaction of the present invention becomes applicable to the analysis based on sequencing-by-hybridization (SBH).

In the above-described method of elongating DNA chains, each of the template DNA fragments may be a cDNA fragment obtained by treating a predetermined RNA with a reverse transcriptase.

By this configuration, the DNA chain elongation reaction of the present invention becomes applicable to gene expression profiling and can proceed it only by simple operations, excluding most part of labor- and time-consuming sample preparation in the general analyses, but using, as the template DNA fragments, cDNA obtained as a reverse-transcription product from genomic DNA or total RNA.

According to the present invention, there is also provided a method of amplifying DNA chains, which includes immobilizing primers for DNA elongation onto a substrate having on the surface thereof a polymer substance which contains a first unit having a group derived from a phosphoester composing the hydrophilic section of a phospholipid, and a second unit having a carboxylic acid-derived group configured by an electron-attractive substitutive group bound to a carbonyl group, heating a reaction system having introduced therein a sample containing template DNA fragments or template RNA fragments having desired sequences, an enzyme system for DNA chain elongation and nucleotide monomers, up to a temperature causing thermal unfolding of the DNA chains (referred to as "thermal unfolding temperature", hereinafter);

cooling the reaction system down to a temperature for annealing (referred to as "annealing temperature", hereinafter);

allowing elongation reaction of the DNA chains to proceed in the reaction system; allowing thermal unfolding of the DNA chains to proceed; and allowing annealing, elongation reaction and thermal unfolding to proceed if necessary, wherein all of these processes are allowed to proceed in the same liquid phase system.

By immobilizing the primers to a predetermined substrate, by annealing the primers with the template DNA fragments, or by hybridizing the template RNA fragments, so as to proceed DNA chain elongation reaction in this way, and by allowing thermal unfolding to proceed after the reaction, the template DNA fragments or template RNA fragments can be released from DNA forming double strands on the substrate, while keeping the single-strand DNA elongated from the primers remained on the substrate, and the template DNA fragments or the template RNA fragments form double-strands with unreacted primers in the next annealing, to thereby proceed the next DNA chain elongation. Repetition of this cycle enables the DNA chain amplifying reaction based on the MPEC process.

Although it has conventionally been necessary for a washing process to remove the DNA fragments or RNA fragments which have not been incorporated into the double strand, there are no DNA fragments nor RNA fragments non-specifically adsorption to the substrate, and this is supposedly contributive to effectively proceed the enzymatic reaction involved in the DNA chain elongation, making it no more necessary to wash the substrate before the elongation reaction.

Although the conventional procedure, involving the individual processes of hybridization, washing, and elongation under addition of enzyme and monomers, was such as allowing the hybridization and the elongation reaction to proceed in separate liquid phases, the present invention makes it possible to proceed the hybridization and the elongation reaction in the same liquid phase.

In this method of amplifying DNA chains, the group derived from phosphoester contained in the first unit of the substrate may be any one of phosphoryl choline group, phosphoryl ethanolamine group, phosphoryl serine group, phosphoryl inositol group, phosphoryl glycerol group, and phosphatidyl phosphoryl glycerol group.

By providing an environment similar to phospholipid onto the surface of the substrate in this way, the DNA chain amplifying reaction can now proceed in an environment similar to the intracellular one. The DNA chain amplification can therefore be proceeded under more milder conditions.

According to the present invention, there is provided a microarray for DNA chain elongation which includes a substrate having on the surface thereof a polymer substance which contains a first unit having a group derived from a phosphoester composing the hydrophilic section of a phospholipid, and a second unit having a carboxylic acid-derived group configured by an electron-attractive substitutive group bound to a carbonyl group, and primers for DNA elongation immobilized onto the surface of the substrate.

By immobilizing the primers to a predetermined substrate, by annealing the primers with the template DNA fragments, or by hybridizing the template RNA fragments, so as to proceed DNA chain elongation reaction in this way, and by allowing thermal unfolding to proceed after the reaction, the template DNA fragments or template RNA fragments can be released from DNA forming double strands on the substrate, while keeping the single-strand DNA elongated from the primers remained on the substrate.

Although it has conventionally been necessary for a washing process to remove the DNA fragments or RNA fragments which have not been incorporated into the double strand, there are no DNA fragments nor RNA fragments non-specifically adsorption to the substrate, and this is supposedly contributive to effectively proceed the enzymatic reaction involved in the DNA chain elongation, making it no more necessary to wash the substrate before the elongation reaction.

Although the conventional procedure, involving the individual processes of hybridization, washing, and elongation under addition of enzyme and monomers, was such as allowing the hybridization and the elongation reaction to proceed in separate liquid phases, the present invention makes it possible to proceed the hybridization and the elongation reaction in the same liquid phase.

In this microarray for DNA chain elongation, the group derived from phosphoester contained in the first unit of the substrate may be any one of phosphoryl choline group, phosphoryl ethanolamine group, phosphoryl serine group, phosphoryl inositol group, phosphoryl glycerol group, and phosphatidyl phosphoryl glycerol group.

By providing an environment similar to phospholipid onto the surface of the substrate in this way, the DNA chain elogation reaction onto the surface of the substrate can now proceed in an environment similar to the intracellular one, and this also contributes to abolish the washing process. The DNA chain amplification can therefore be proceeded under more milder conditions.

According to the present invention, it is made possible to produce double strands by allowing the elongation reaction of DNA chains to proceed on the DNA microarray, and then to keep single strand DNA remained on the substrate of the DNA microarray by thermal unfolding.

BRIEF DESCRIPTION OF THE DRAWINGS

The above and other objects, advantages and features of the present invention will be more apparent from the following description taken in conjunction with the accompanying drawings.

BEST MODES FOR CARRYING OUT THE INVENTION

Embodiments of the present invention will be detailed below.

(First Embodiment)

Figure 1:
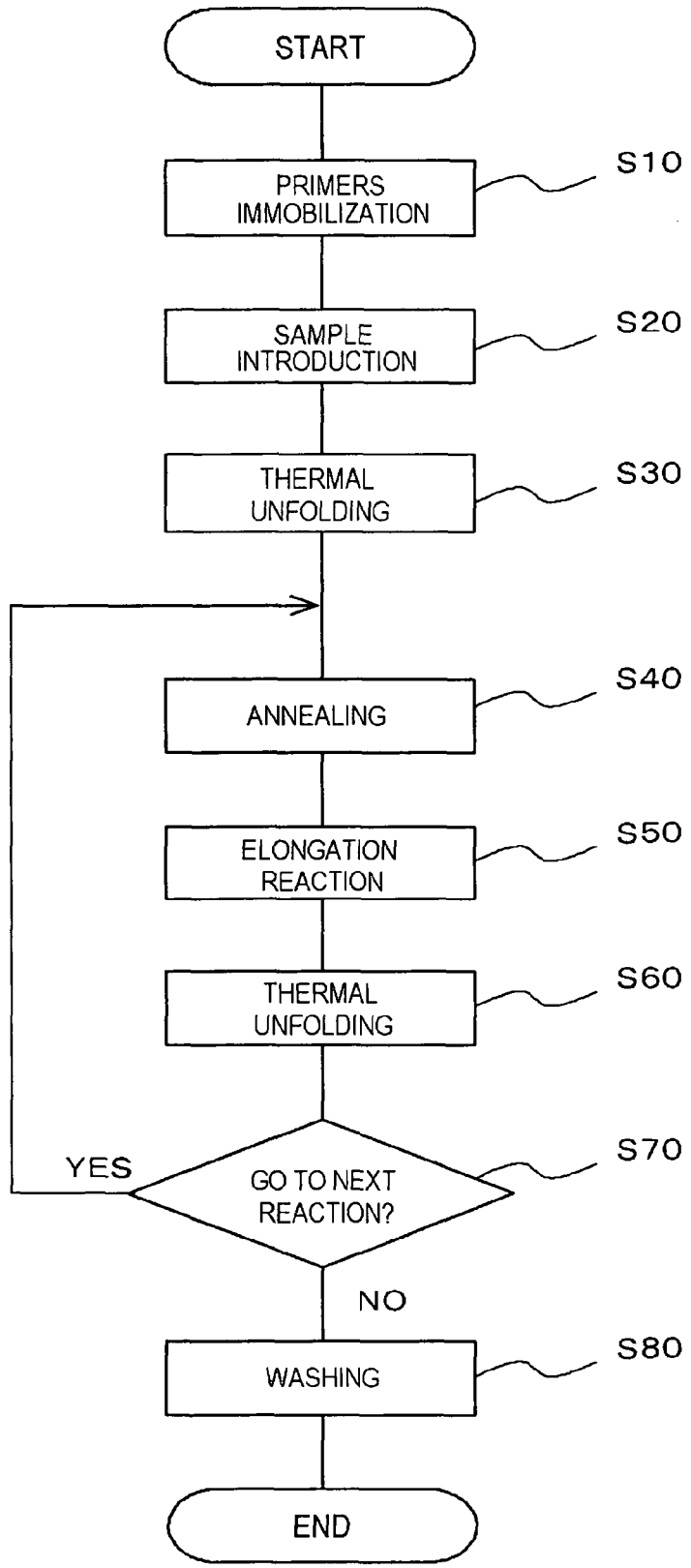
FIG. 1 is a flow chart showing a method of amplifying DNA chains according to a first embodiment of the present invention.

FIG. 1 is a flow chart showing procedures of the method of amplifying DNA chains as the first embodiment.

The method of amplifying DNA chains is such as immobilizing primers for DNA amplification (referred to as "primers", hereinafter) onto a substrate having on the surface thereof a polymer substance which contains a first unit having a group derived from a phosphoester composing the hydrophilic section of a phospholipid, and a second unit having a carboxylic acid-derived group configured by an electron-attractive substitutive group bound to a carbonyl group (step S10); heating a reaction system having introduced therein a sample containing template DNA fragments or template RNA fragments having desired sequences, an enzyme system for DNA chain elongation and nucleotide monomers, up to a temperature causing thermal unfolding of the DNA chains (referred to as "thermal unfolding temperature", hereinafter) (step S30); cooling the reaction system down to a temperature for annealing (referred to as "annealing temperature", hereinafter) (step S40); allowing elongation reaction of the DNA chains to proceed in the reaction system (step S50); allowing thermal unfolding of the DNA chains to proceed (step S60); and allowing annealing, elongation reaction and thermal unfolding to proceed if necessary (repetition of step S40 to step S60). All of these processes are allowed to proceed in the same liquid phase system.

Figure 2:
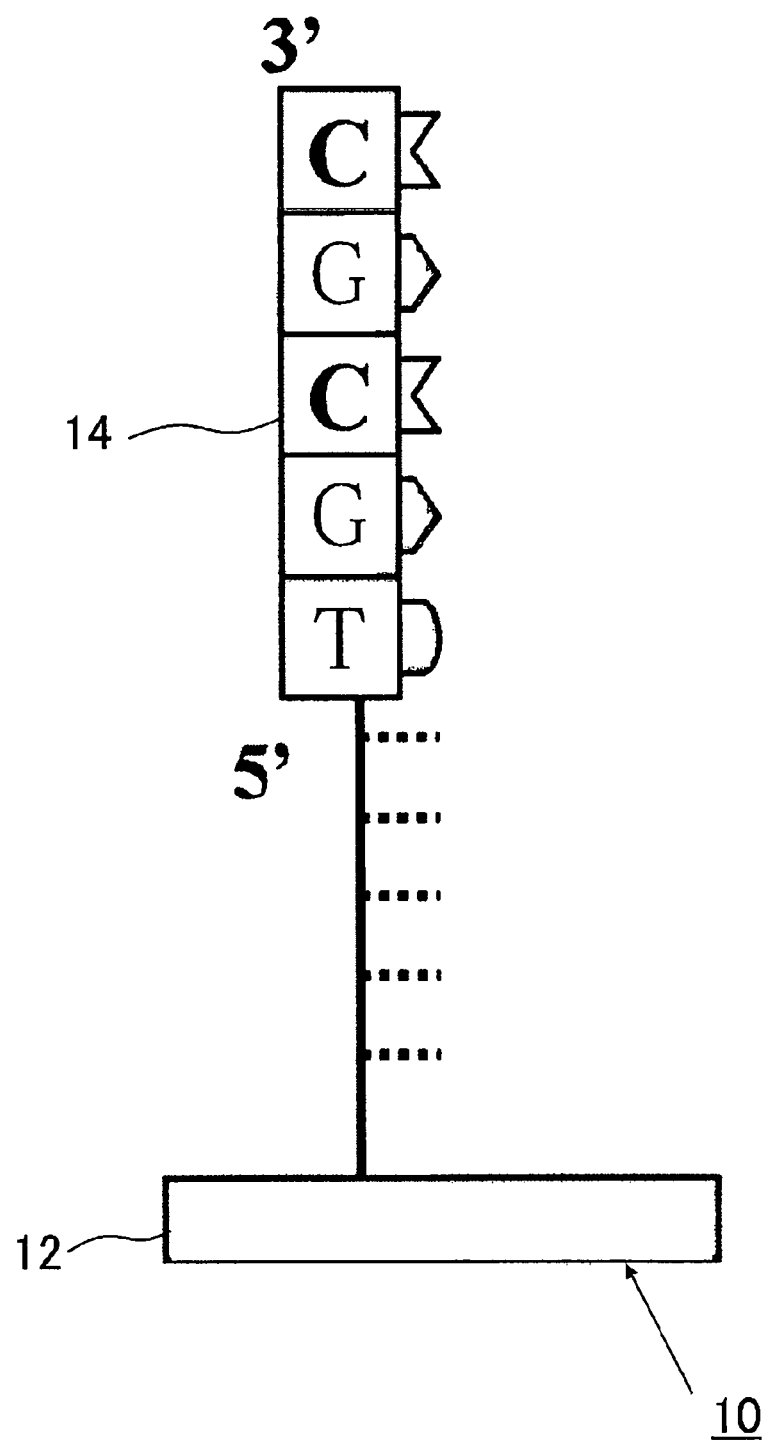
FIG. 2 is a drawing schematically showing a part of a DNA microarray used in the first embodiment.

In step S10, as shown in FIG. 2, a primer 14 for DNA amplification is immobilized onto the surface of a substrate 12.

The surface of substrate used herein is configured so that a polymer substance, which contains a first unit having a group derived from a phosphoester composing the hydrophilic section of a phospholipid, and a second unit having a carboxylic acid-derived group, reside on the surface thereof.

The polymer substance, containing the first unit having a group derived from a phosphoester composing the hydrophilic section of a phospholipid, and the second unit having a carboxylic acid-derived group, is a polymer having both properties of suppressing non-specific adsorption of the DNA chains, and of allowing immobilization of the DNA chains. In particular, the group contained in the first unit, and the group derived from a phosphoester composing the hydrophilic section of a phospholipid plays a role of suppressing non-specific adsorption of the template DNA fragments, and the carboxylic acid-derived group contained in the second unit plays a role of chemically immobilizing the primers. More specifically, the primers are immobilized onto the surface of the substrate, through a covalent bond formed at the site of a carboxylic acid-derived group of a coating layer composed of the polymer substance.

The first unit may be configured as having a group such as (meth)acryloyloxyalkyl phosphorylcholine groups such as 2-methacryloyloxyethylphosphoryl choline group, 6-methacryloyloxyhexylphosphoryl choline group; (meth)acryloyloxyalkoxyalkylphosphoryl choline groups such as 2-methacryloyloxyethoxyethylphosphoryl choline group and 10-methacryloyloxyethoxynonyl phosphoryl choline group; and alkenylphosphoryl choline groups such as allylphosphoryl choline group, butenylphosphoryl choline group, hexenylphosphoryl choline group, octenylphosphoryl choline group, and decenylphosphoryl choline group; having a phosphoryl choline group contained in these groups.

Of these groups, 2-methacryloyloxyethylphosphoryl choline is preferable. By composing the first unit as having 2-methacryloyloxyethylphosphoryl choline, the non-specific adsorption of the template DNA fragment onto the surface of the substrate can be suppressed in a more strict manner.

Although the phosphoryl choline groups having a basic skeleton expressed by formula (a) below were exemplified in the above, the phosphoryl choline group may be replaced by the phosphoryl ethanolamine group expressed by formula (b) below, phosphoryl inositol group expressed by formula (c) below, phosphoryl serine group expressed by formula (d) below, phosphoryl glycerol group expressed by formula (e) below, and phosphatidyl phosphoryl glycerol expressed by formula (f) below (the same will apply also to the description hereinafter).

(Chemical Formula 1)

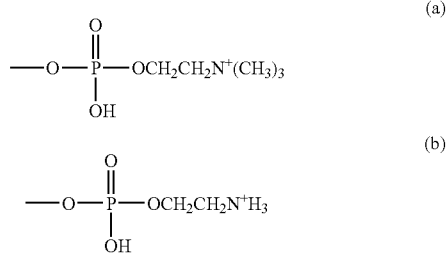

-continued

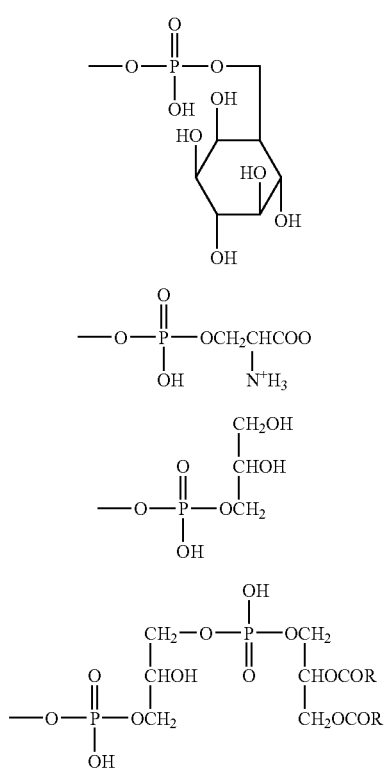

The carboxylic acid derivative is a substance having an activated carboxyl group of a carboxylic acid, and is a carboxylic acid having a leaving group bound to C=O. The carboxylic acid derivative is, more specifically, a compound having a group of higher electrowithdrawing property than the alkoxyl group, as being enhanced in the nucleophilic reactivity. The carboxylic acid-derived group is a compound showing reactivity against amino group, thiol group, hydroxyl group and so forth.

The carboxylic acid derivative can further specifically be exemplified by compounds in which the carboxyl group(s) of carboxylic acids, such as acrylic acid, methacrylic acid, crotonic acid, maleic acid, fumaric acid and the like, are converted into acid anhydride, acid halide, activated ester, activated amide or the like. The carboxylic acid-derived group is an activated group derived from such compounds, and may have a group including activated esters such as p-nitrophenyl group and N-hydroxysuccinimide; halogens such as —Cl and —F; and so forth.

The carboxylic acid-derived group may be a group expressed by the formula (1) below.

(Chemical Formula 2)

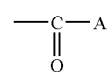 (1)

(where, in the above-described formula (1), A is a leaving group excluding hydroxyl group.)

A monovalent group expressed by the above-described formula (1) may be either of the groups selected from those expressed by the formulae (p) and (q) below.

(Chemical formula 3)

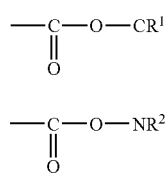

(where, in the above-described formulae (p) and (q), each of $R^1$ and $R^2$ independently expresses a monovalent organic group which may be any of those of linear chain, branched and cyclic ones. In the above-described formula (p), $R^1$ may be a divalent group capable of forming a ring together with C. In the above-described formula (q), $R^2$ may be a divalent group capable forming a ring together with N.)

As the group expressed by the above-described formula (p) those expressed typically by the formulae (r), (s) and (w) below can be exemplified. As the group expressed by the above-describe formula (q), the group expressed by the formula (u) below can be exemplified.

The groups expressed by the above-described formula (1) may typically be any one of groups derived from acid anhydrides expressed typically by the formula (r) and the formula (s) below; group derived from acid halide expressed by the formula (t) below; groups derived from activated esters expressed by the formula (u) and the formula (w) below; and group derived from activated amide expressed by the formula (v) below.

(Chemical Formula 4)

-continued

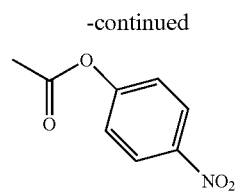

(w)

Of the carboxylic acid-derived groups, the activated ester group is preferably used by virtue of its excellence in the reactivity under mild conditions. The mild conditions can be exemplified by neutral or alkali conditions, specifically expressed by pH7.0 or above and 10.0 or below, more specifically pH7.6 or above and 9.0 or below, and still more specifically pH8.0.

The "activated ester group" specified in this specification is not strictly specified in the definition thereof, but the term is generally used as a technical expression in the fields of various chemical syntheses including polymer chemistry and peptide synthesis, as indicating ester groups having any highly acidic electrowithdrawing group on the alcohol side of ester group, and capable of activating nucleophilic reaction, that is, as indicating highly reactive ester groups. In the field of peptide synthesis, as described in "Pepuchido Gosei no Kiso to Jikken (Basics and Experiments of Peptide Synthesis)", co-written by Nobuo IZUMIYA, Tetsuo KATO, Haruhiko AOYAGI, and Michinori WAKI, 1985, published by Maruzen Co., Ltd., the activated ester process is used as one method of activating the C-terminal of amino acid or peptide.

In practice, it is an ester group having an electrowithdrawing group on the alcohol side of ester group, and is activated to a degree larger than alkyl ester. The activated ester group has a reactivity against groups including amino group, thiol group and hydroxyl group. Still more specifically, phenol esters, thiophenol esters, N-hydroxylamine esters, cyanomethyl ester, esters of heterocyclic hydroxyl compounds and so forth are known as the activated ester groups having far higher reactivity as compared with alkyl esters or the like.

The explanation herein will be made on the case where the activated carboxylic acid derivative group in the polymer substance is the activated ester group. p-Nitrophenyl group, N-hydroxysuccinimide group, succinimide group, phthalimide group, 5-norbornene-2,3-dicarboximide and so forth can be exemplified as the activated ester group, wherein p-nitrophenyl group for example is preferably used.

For the substrate, on the surface of which the primers will be immobilized, a further specific example of combination of the first unit and the second unit may be such that the first unit, containing a group derived from a phosphoester composing the hydrophilic section of a phospholipid, has 2-methacryloyloxyethylphosphoryl choline group, and that the activated ester group is p-nitrophenyl group.

The polymer substance used for a coating layer on the substrate of this embodiment may contain other group, besides the group derived from a phosphoester composing the hydrophilic section of a phospholipid and carboxilic acid. The polymer substance may be a copolymer. More specifically, the polymer substance is preferably a copolymer containing butyl methacrylate group. This configuration makes the polymer substance appropriately hydrophobic, and ensures a further desirable level of adsorptivity of the polymer substance to the surface of the substrate.

More specifically, the polymer substance may be a copolymer of a first monomer having a 2-methacryloyloxyethylphosphoryl choline (MPC) group, a second monomer having p-nitrophenyloxycarbonyl polyethylene glycol methacrylate (NPMA) group, and a third monomer having a butyl methacrylate (BMA) group. A copolymer of these monomers poly (MPC-co-BMA-co-NPMA) (PMBN) can schematically be expressed by the general formula (2) below.

{Chemical Formula 5}

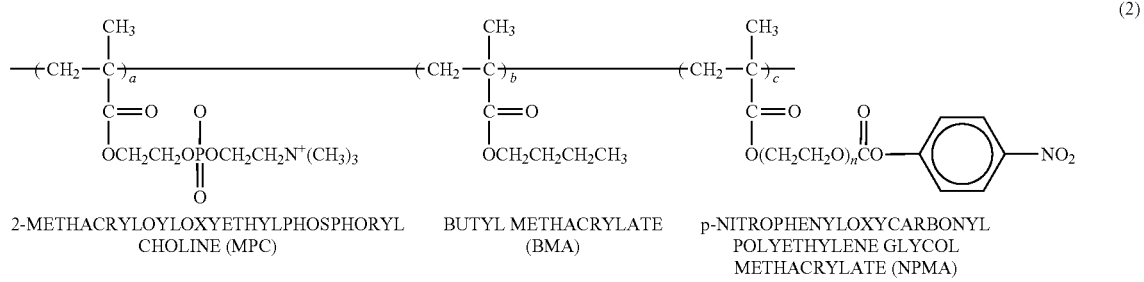

In the above-described general formula (2), each of a, b and c independently expresses a positive integer. In the above-descried general formula (2), the first to third monomers may be copolymerized on the block basis, or may randomly be copolymerized.

The copolymer expressed by the above-described general formula (2) is configured so as to attain more excellent balance of imparting the polymer substance with an appropriate level of hydrophobicity, a performance of suppressing non-specific adsorption of the template DNA fragment, and a performance of immobilizing the primers. For this reason, by using thus-configured copolymer, it is made possible to cover the surface of the substrate with the polymer substance in a more exact manner, and to immobilize the primers in a more exact manner through a covalent bond to thereby introduce them onto the substrate, while suppressing non-specific adsorption of the template DNA fragments onto the substrate having the polymer substance coated thereon.

The copolymer expressed by the above-described general formula (2) can be obtained by mixing the individual monomers of MPC, BMA and NPMA, according to any publicly-known method of polymerization, such as radical polymerization. For the case where the copolymer expressed by the above-described general formula (2) is prepared by radical polymerization, solution polymerization may be proceeded in an inert gas atmosphere such as Ar or the like, under a temperature condition of 30° C. or above and 90° C. or below.

Solvent adopted to the solution polymerization may appropriately be selected, wherein any one of, or a plurality of organic solvents, including alcohols such as methanol, ethanol and isopropanol, ethers such as diethyl ether, and chloroform, may be used independently or in combination. More specifically, an 8:2 mixed solvent of diethyl ether and chloroform may be used.

Radical polymerization initiator used for the radical polymerization may be any of those used generally. Applicable examples include azo-base initiators such as azobis (isobutyronitrile) (AIBN) and azobis (valeronitrile); and oil-soluble organic hyperoxides such as lauroyl peroxide, benzoyl peroxide, t-butyl peroxy neodecanoate and t-butyl peroxy pivalate.

Still more specifically, the polymerization can be proceeded using a mixed solvent of diethyl ether and chloroform having a volume ratio of 8:2 and AIBN, in Ar, at 60° C. for 2 to 6 hours or around.

This embodiment has described an exemplary case where the polymer substance has the third unit containing a butyl methacrylate group, wherein, assuming now that the polymer substance which contains the first unit having a group derived from a phosphoester composing the hydrophilic section of a phospholipid, and the second unit which contains a carboxylic acid-derived group as a first polymer substance, the substrate may contain, in addition to this, a second polymer substance which contains a first unit having a group derived from a phosphoester composing the hydrophilic section of a phospholipid, and a third unit which contains a butyl methacrylate group.

The first unit of the first polymer substance and the first unit of the second polymer substance may have the same structure or different structures. For the case where the above-described first polymer substance contains the third unit which contains a butyl methacrylate group, the third unit of the first polymer substance and the third unit of the second polymer substance may have the same structure or different structures.

Thus-configured second polymer substance is used as a polymer capable of suppressing non-specific adsorption of the template DNA fragments. For example, MPC polymer (from NOF Corporation) containing 30 mol % of phosphoryl choline group and 70 mol % of butyl methacrylate group can be used as this sort of polymer.

For the case where the polymer substance is composed of the above-described first polymer substances and the second polymer substance, these polymer substances may be configured as a mixture. The polymers of the individual polymer substances can be dissolved, for example, into ethanol solution, so that a mixed polymer can readily be obtained by mixing the individual polymer solutions.

The substrate having a coating layer composed of the above-described polymer substance(s) formed on the surface thereof can be obtained by coating a liquid containing the polymer substance(s) onto the surface of the substrate formed in a predetermined geometry, and by drying the liquid. It is also allowable to dip the substrate into a liquid containing the polymer substance(s), and then to dry the liquid.

Adoption of a plastic material as the substrate is preferable in view of ensuring flexibility to alteration in the geometry and size, and provision at lower cost as compared with the glass substrate. As this sort of plastic material, thermoplastic resin is adoptable in view of their ease in the surface treatment and mass-producibility.

As the thermoplastic resin, those emitting only a small energy of fluorescence are adoptable. Use of the resin emitting only a small energy of fluorescence can lower the background level in the reaction for detecting the DNA chains, so that the detection sensitivity can further be improved. Linear chain polyolefins such as polyethylene and polypropylene; cyclic polyolefins; fluorocarbon resins and so forth can be used as the thermoplastic resin less in the energy of fluorescence emission. Of these resins, saturated cyclic polyolefin is especially excellent in the heat resistance, chemical resistance, low fluorescence emission, transparency and moldability, suitable for optical analysis, and preferably used as a material composing the substrate.

The saturated cyclic polyolefin herein means a saturated polymer obtained by hydrogen addition of a homopolymer having a cyclic olefin structure, or a copolymer of cyclic olefin and α-olefin. The former is exemplified by saturated polymers manufactured by ring-opening polymerization of norbornene-base monomers represented by norbornene, dicyclopentadiene and tetracyclododecene, and alkyl-substituted products thereof, for example. The latter copolymer is a saturated polymer manufactured by hydrogen addition of random copolymers of α-olefin such as ethylene, propylene, isopropylene, 1-butene, 3-methyl-1-butene, 1-pentene, 3-methyl-1-pentene, 1-hexene and 1-octene, and cyclic olefin-base monomer. The copolymer is preferably those containing ethylene. These resins may be used independently, or may be copolymer or mixture of two or more species thereof. It is also allowable to use not only saturated cyclic polyolefins obtainable by ring-opening polymerization of monomers having a cyclic olefin structure, but also a saturated cyclic polyolefin obtainable by addition polymerization of monomers having a cyclic olefin structure.

The substrate, composed of a plastic material containing the above-described polymer substance in the surficial portion thereof, can be obtained by coating a liquid containing the polymer substance onto the surface of the substrate formed in a predetermined geometry, and by drying the liquid. It is also allowable to dip the substrate into a liquid containing the polymer substance(s), and then to dry.

When plastic is selected as a material composing the substrate, the geometry of the substrate is not limited to plate, but may be film or sheet, for example. More specifically, the substrate may be a flexible plastic film. The substrate may be configured by a single component, or by a plurality of components.

Next paragraphs will explain a method of immobilizing the primers onto the surface of the substrate.

For example, (i) the primers can be immobilized onto the surface of the substrate, by allowing at least a part of activated ester groups, out of a plurality of activated ester groups contained in the polymer substance on the substrate, to react with the primers so as to form covalent bonds, to thereby immobilize the primers onto the surface of the substrate, and then (ii) the primers can be immobilized onto the surface of the substrate by inactivating the activated ester groups on the surface of the substrate, other than those having the primers immobilized thereon, that is, by inactivating the residual activated ester groups. Paragraphs below will explain the individual process steps.

When the primers to be annealed with the template DNA fragments are immobilized onto the substrate in the above-described process step (i), it is preferable to adopt a method of spotting a liquid containing the primers dissolved or dispersed therein. A part of the activated ester groups contained in the polymer substance react with the primers, so as to form covalent bonds with the primers.

The liquid containing the primers dissolved or dispersed therein may be typically neutral to alkali, typically expressed by pH7.6 or above.

After the spotting, the substrate may be washed with pure water or buffer solution, so as to remove the primers not immobilized onto the surface of the substrate.

As shown in the above-described process step (ii), after the washing, the activated esters on the surface of the plastic substrate, remained as having no primers immobilized thereon, are inactivated using an alkali compound or a compound having a primary amino group.

Applicable examples of the alkali compound include sodium hydroxide, potassium hydroxide, sodium carbonate, sodium hydrogen carbonate, disodium hydrogen phosphate, calcium hydroxide, magnesium hydroxide, sodium borate, lithium hydroxide and potassium phosphate.

As the compounds having primary amino group, applicable examples include glycine, 9-amino aquazine, aminobutanol, 4-aminobutylic acid, aminocaprylic acid, aminoethanol, 5-amino-2,3-dihydro-1,4-pentanol, aminoethanethiol hydrochloride, aminoethanethiol sulfate, 2-(2-aminoethylamino)ethanol, 2-aminoethyl dihydrogen phosphate, hydrogen aminoethyl sulfate, 4-(2-aminoethyl)morpholine, 5-aminofluorescein, 6-aminohexanoic acid, aminohexyl cellulose, p-aminohippuric acid, 2-amino-2-hydroxymethyl-1,3-propanediol, 5-aminoisophthalic acid, aminomethane, aminophenol, 2-aminooctane, 2-aminooctanoic acid, 1-amino-2-propanol, 3-amino-1-propanol, 3-aminopropene, 3-aminopropionitrile, aminopyridine, 11-aminoundecanoic acid, aminosalicylic acid, aminoquinoline, 4-aminophthalonitrile, 3-aminophthalimide, p-aminopropiophenone, aminophenylacetic acid, and aminonaphthalene. Of these, aminoethanol and glycine are preferably used.

It is preferable that the primers to be immobilized onto the substrate have an amino group preliminarily introduced therein, for the purpose of enhancing reactivity with the activated ester group. Because amino group is excellent in reactivity with the activated ester group, adoption of the primer having an amino group introduced therein allows efficient and tight immobilization of the primers onto the surface of the substrate. The position of introduction of amino group may be at the terminal of the molecular chain or in the side chain, wherein introduction at the terminal of the molecular chain is preferable, in view of allowing more efficient annealing with complementary template DNA fragments.

By the above-described processes, a microarray for DNA chain elongation which includes a substrate having on the surface thereof a polymer substance which contains a first unit having a group derived from a phosphoester composing the hydrophilic section of a phospholipid, and a second unit having a carboxylic acid-derived group configured by an electron-attractive substitutive group bound to a carbonyl group, and primers for DNA amplification immobilized onto the surface of the substrate, that is, the DNA microarray 10 having the primer 14 immobilized on the surface of the substrate 12 a shown in FIG. 2, can be obtained.

Referring now back to FIG. 1, in step S20, a sample containing template DNA fragments 16 for DNA chain elongation, to be annealed with the primers 14 immobilized onto the surface of the substrate 12 of the DNA microarray 10 obtained in step S10, an enzyme system for DNA chain elogation, and nucleotide monomers, is introduced. It is to be noted that similar operations and effects can be obtained if template RNA fragments are used in place of the DNA fragments, as templates used for DNA amplification.

As the reaction system composed of thus-introduced sample, an MPEC buffer containing nucleotide monomers (dATP, dCTP, dGTP, dTTP, etc.) under the presence of either of DNA polymerase or DNA ligase as the enzyme system for DNA chain elongation, for the case where DNA fragments are used as the templates and under the presence of either of reverse transcriptase, or a combination of DNA ligase and reverse transcriptase as the enzyme system for DNA chain elongation, for the case where RNA fragments are used as the templates Among the DNA polymerases, TaqDNA polymerase, TthDNA polymerase, PfuDNA polymerase and so forth, which are particular DNA polymerases derived from heat-resistant bacteria, are applicable.

At least one species of the nucleotide monomers may be labeled. For example, by using Cy3-dUTP having a fluorescence label at 3-position of the base of dTTP as the nucleotide monomers, the Cy3-dUTP is inserted at positions on the elongation (primer) side corresponded to adenine (A) in the template DNA fragments. By this process, the DNA fragments produced from the primers, which undergo the elongation reaction, are dyed with fluorescence of Cy3-dUTP, and the DNA fragments become detectable.

It is also allowable to label other nucleotide monomers, or to label a plurality of species of the nucleotide monomers. Besides introduction of the fluorescent substance, the DNA chains can be detected also by introduction of photo-absorbing substances, methods of radioactive labeling ($P^{32}$-ATP, $P^{32}$-dATP), non-radioactive labeling such as enzymatic labeling and so forth.

In the method of enzymatic labeling, DNA can be detected by elongating the primers using biotin-bound, or digoxigenin (DIG: steroidal natural product)-bound nucleic acid (for example, biotin-dUTP, DIG-dUTP), treating them with a fluorescence-labeled alkali phosphatase or with alkali phosphatase, and allowing them to react with nitroblue tetrazolium (NBT) in a 5-bromo-4-chloro-3-indolyl phosphate (BCIP) solution for several hours.

In step S30, temperature of the reaction system having the sample introduced therein is elevated up to the thermal unfolding temperature of the DNA chains (melting temperature: Tm) or above, typically up to 90° C. to 95° C. By the thermal unfolding, the template DNA fragments having a folded structure which is found in auto-complementary chain and the primers are stretched to give straight single strands.

Figure 3:
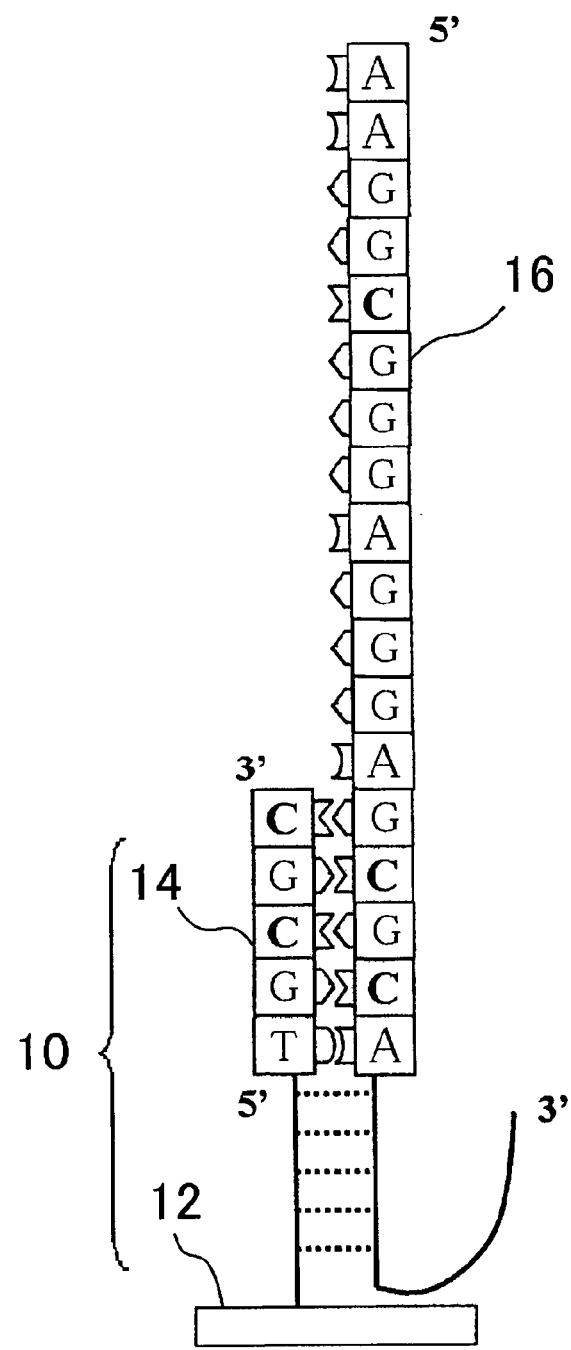
FIG. 3 is a drawing showing a state of annealing of a template DNA to the primer on the DNA microarray (the 18-mer sequence is SEQ ID NO:6)

Next in step S40, the temperature of the reaction system is lowered to the temperature where the primers and the template DNA fragments are annealed (annealing temperature), typically down to 4° C. to 65° C., and preferably down to 50° C. to 65° C. By the annealing, the primers having a sequence complementary to a part of the template DNA fragments and such template DNA fragments form double strands (FIG. 3). The reaction system is directly brought into step S50, without carrying out washing.

In this stage, it has been necessary for a washing process in the conventional process to remove any DNA fragments (or RNA fragments) failed in forming the double strands after the annealing and before the elongation reaction, whereas in this embodiment, there are no DNA fragments (or RNA fragments) non-specifically adsorbed onto the substrate, and this supposedly allows the enzymatic reaction relevant to the DNA chain elongation to proceed in an efficient manner, and makes washing of the substrate no more necessary. The hybridization and the elongation reaction have been proceeded in separate liquid phases, such that the individual processes are carried out in the order of hybridization, washing, and elongation under addition of an enzyme and monomers, whereas in this embodiment, the hybridization and the elongation reaction can be proceeded in the same liquid phase, in other words, the reaction system can be used without modification.

Figure 4:
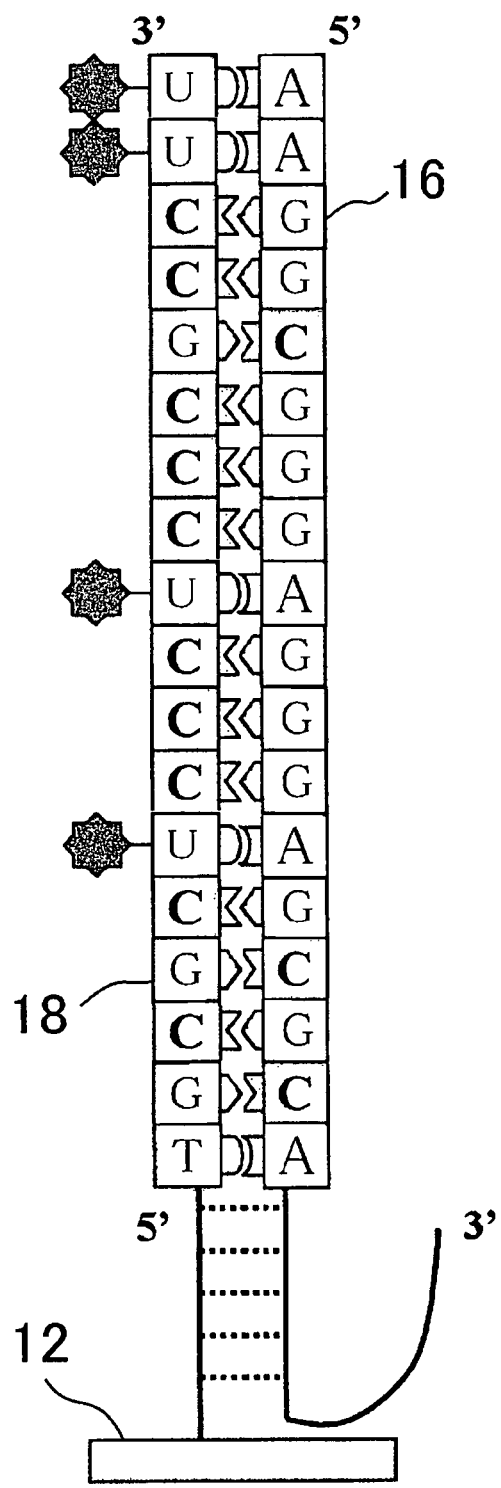
FIG. 4 is a drawing showing a state of the elongation reaction of the DNA chain on the primer (the sequence complementary to SEQ ID NO:6 is SEQ ID NO:7)

In step S50, the temperature of the reaction system in which the annealing was completed is controlled so as to gradually elevate from the annealing temperature up to the thermal unfolding temperature. In other words, the temperature of the reaction system is controlled as being adjusted to a predominent temperature between the annealing temperature and the thermal unfolding temperature, typically at 65° C. to 75° C. By controlling the temperature of the reaction system in this way, the elongation reaction of the DNA chains based on the MPEC process can proceed, that is, the DNA fragments complementary to the template DNA fragments 16 are formed on the substrate so as to give double-strand DNA (FIG. 4).

Although the exemplary case shown herein was such as using a heat resistant DNA polymerase with respect to the template DNA fragments, there is no special limitation on the enzyme so far it is capable of synthesizing new DNA chain using the DNA chains as the template. Examples of such DNA polymerase include Pol-I DNA polymerase (*Escherichia coli* DNA polymerase I, Klenow fragment, etc.), type-α DNA polymerase (DNA polymerase derived from *Pyrococcus friosus*, VENT DNA polymerase, KOD DNA polymerase, and DEEP VENT DNA polymerase) and non-α-non-Pol-I DNA polymerase (DNA polymerase described in WO97/24444).

Also use of a DNA ligase, in place of the DNA polymerase, allows the DNA chain elongation reaction to proceed, and therefore allows the DNA chain amplification to take place.

For the case where the template RNA fragments are used, the DNA chains can be elongated on the primer side, by allowing the primers on the substrate to directly act on the template RNA fragments, and by using a reverse transcriptase. The DNA chain can be elongated on the primer side, also by allowing a reverse transcriptase to act on the template RNA fragments so as to once synthesize the cDNA (complementary DNA) (first chain synthesis), and then by allowing the DNA polymerase or the DNA ligase to act thereon.

Figure 5:
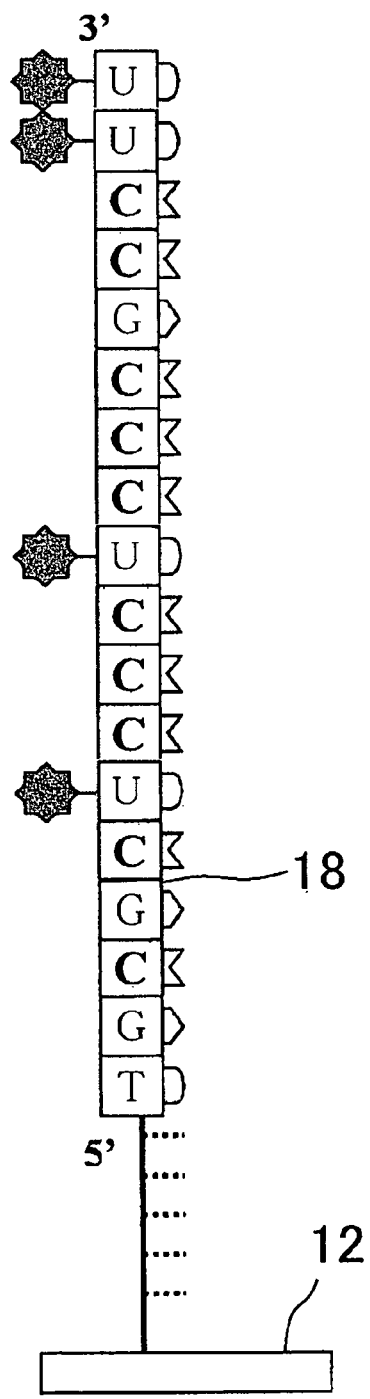
FIG. 5 is a drawing showing a state of unfolding of the resultant double strand after the elongation reaction (the sequence shown is SEQ ID NO:7)

Referring now back to FIG. 1, in step S60, the reaction system after the elongation reaction is maintained at the thermal unfolding temperature of the DNA chain, typically at 90° C. to 95° C. By the thermal unfolding, the template DNA fragments 16 are released from the double-strand DNA on the surface of the substrate (FIG. 4), to thereby leave the single-strand DNA fragments 18 (FIG. 5).

In step S70, whether the process should advance to the next elongation reaction or not is judged. The judgment may automatically be made based on whether a specified number of times of repetition of the reaction, set by using a temperature regulator (thermo-cycler) or the like, was reached or not, or may be made every time based on the operator's judgment.

If the result of judgment was YES, that is, when the process was judged to advance to the next elongation reaction, the process returns back to step S40, wherein the annealing (step S40), elongation reaction (step S50) and thermal unfolding (step S60) are repeated so as to proceed the DNA elongation reaction using the unreacted primers. By repeating this cycle 1 to 50 times, the DNA chains are amplified on the substrate based on the MPEC process.

If the result of judgment in step S70 was NO, that is, when the process was not judged to advance to the next elongation reaction, the process goes to step S80, wherein the reaction solution is discarded, and the DNA microarray is washed using, for example, a 0.1 wt % SDS solution, so as to finish the process.

For the DNA chain amplification, it is preferable to provide a plurality of spots within a certain section, wherein each of the spots having the primers immobilized thereto, so as to form a microarray.

The length of the primers for DNA amplification, to be immobilized onto the surface of the substrate, can arbitrarily be determined depending on purposes and applications, and can typically be determined as 5 to 50 bases.

(Second Embodiment)

Figure 6:
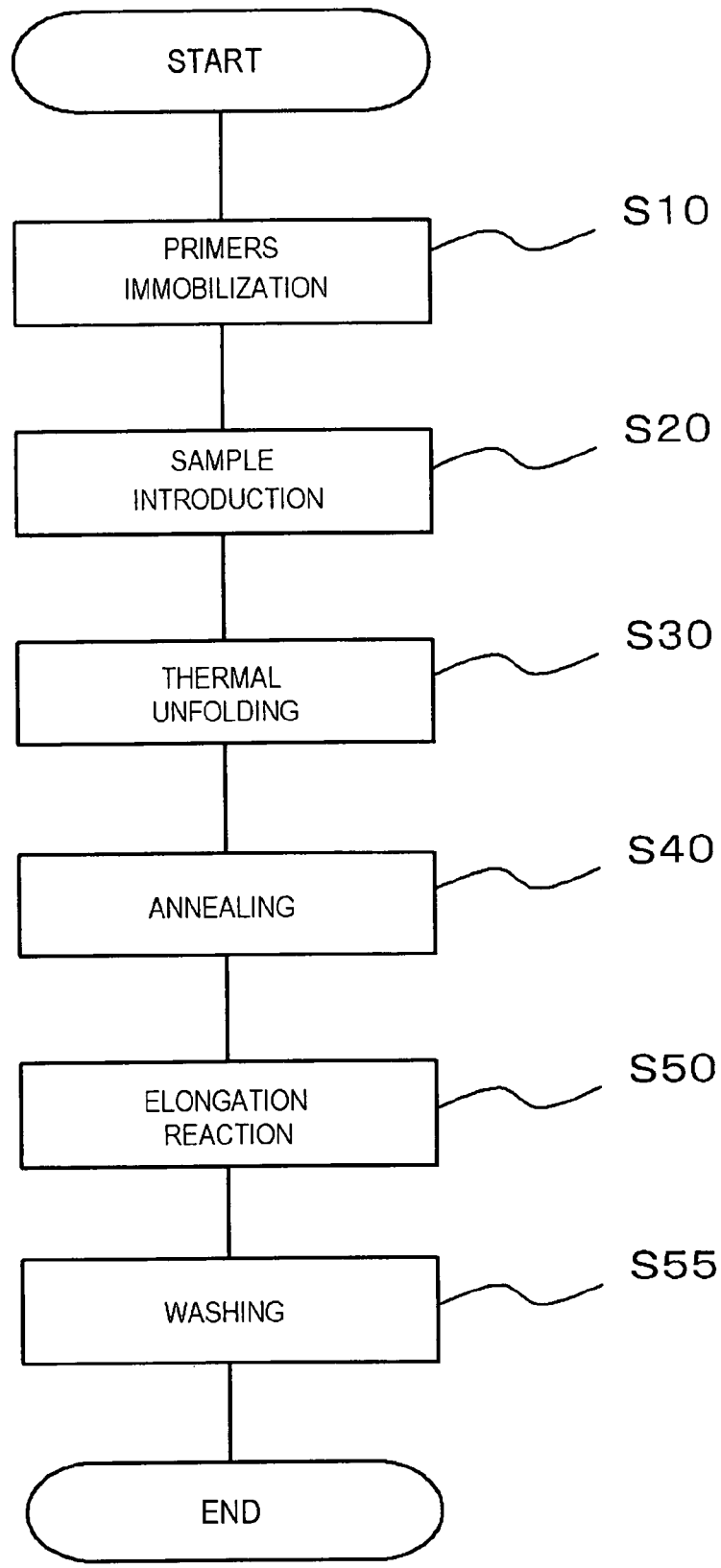
FIG. 6 is a flow chart showing a method of elongating DNA chains according to a second embodiment of the present invention.

FIG. 6 is a flow chart showing procedures of a method of elongating DNA chains as a second embodiment. In FIG. 6, any procedures similar to those shown in FIG. 1 will be given with the same reference numerals, so as to avoid repetitive explanation.

The method of elongating DNA chains is such as immobilizing primers for DNA elongation (simply referred to as "primers", hereinafter) onto a substrate having on the surface thereof a polymer substance which contains a first unit having a group derived from a phosphoester composing the hydrophilic section of a phospholipid, and a second unit having a carboxylic acid-derived group configured by an electrowithdrawing substitutive group bound to a carbonyl group (step S10); heating a reaction system having introduced therein a sample containing template DNA fragments or template RNA fragments having desired sequences, an enzyme system for DNA chain elongation and nucleotide monomers, up to a temperature causing thermal unfolding of the DNA chains (step S30); cooling the reaction system down to a temperature for annealing (step S40); and allowing elongation reaction of the DNA chains to proceed in the reaction system (step S50); wherein all of these processes are allowed to proceed in the same liquid phase system.

As described in the above, in step S20, a sample containing template DNA fragments for DNA chain elongation, to be annealed with the primers immobilized onto the surface of the substrate, and nucleotide monomers, is introduced, wherein the sample and the reaction system having the sample introduced therein may be same as those described in the above.

After the elongation reaction in step S50, the reaction solution is discarded, and the DNA microarray is washed using, for example, a 0.1 wt % SDS solution, so as to finish the process.

Exemplary applications of the method of elongating DNA chains of this embodiment will be explained below.

(SNP Analysis)

Assuming a sequence complementary to a base sequence containing a characteristic sequence of a predetermined target gene as a completely-matched sequence, SNP analysis can be carried out by using primers having a sequence obtained by replacing one base of the completely-matched sequence with other base. Each primer preferably has a length of 25 bases or shorter.

More specifically, in step S10, DNA fragments each having a characteristic sequence of a target gene with only one mismatched base are immobilized as the primers onto the surface of the substrate. In this process, a 384-well (256 spots/well) or 96-well (1024 spots/well) microarray is used, and the sequences of the primers immobilized in the individual spots are memorized. The sample is introduced in step S20, while using the DNA chains containing the characteristic sequence as the template DNA fragments, the thermal unfolding is carried out in step S30, and annealing is proceeded in step S40. In step S50, the elongation reaction proceeds only on the primers existing in a form of double strand having the template DNA chains annealed therewith.

As described in the above, by preliminarily incorporating the labeled nucleotide monomers into the sample to be introduced in step S20, the DNA fragments obtained from the primers by the elogation reaction are labeled, the spots containing the fluorescent DNA fragments remained on the substrate after the washing in step S55 can be detected, thereby the sequences of the primers immobilized to the detected spots can be known, because the sequences of the primers immobilized to the individual arrays are memorized. In this way, the base sequences of the primers causing thereon the elongation reaction can be known, and it is therefore made possible to analyze single nucleotide polymorphism with respect to the template DNA fragments containing the characteristic sequence of the target gene.

(SBH Analysis)

Base sequencing by hyblidization (SBH) analysis will be accessible by preparing a complete set of primers each having a sequence of a predetermined number of bases, 6 to 10 mer for example and preferably 8 mer, is obtained, which accounts for $4^8=65536$ species when 8-mer primers are used, and by immobilizing each of the individual primers into a single spot.

More specifically, the individual primers are immobilized into the individual spots of the microarray in step S10. In this process, the sequences of the primers immobilized into the individual spots are memorized. Then in step S20, a sample is introduced while using DNA fragments having unknown base sequences as the template DNA fragments, thermal unfolding is carried out in step S30, and annealed in step S40. In step S50, the elongation reaction proceeds only on the primers existing in a form of double strand having the template DNA chain fragments annealed therewith.

As described in the above, by preliminarily incorporating the labeled nucleotide monomers into the sample to be introduced in step S20, the DNA fragments obtained from the primers are labeled, and the spots containing the fluorescent DNA fragments remained on the substrate after the washing in step S55 can be detected, thereby the sequences of the primers immobilized to the detected spots can be known, because the sequences of the primers immobilized to the individual arrays are memorized. In this way, the base sequences of the primers causing thereon the elongation reaction can be known.

Figure 7:
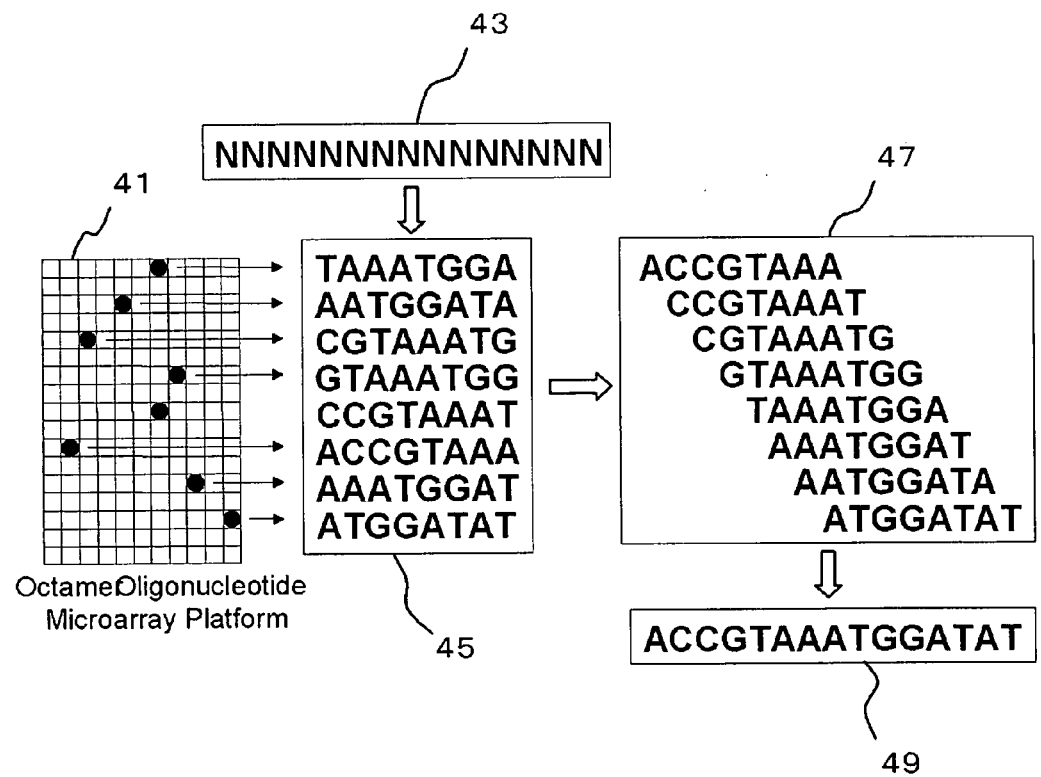
FIG. 7 is a drawing showing an exemplary application of the second embodiment (the 15-mer sequence is SEQ ID NO:8)

Now as shown in FIG. 7, the spots causing the elongation reaction on a substrate 41, the individual sequences in a random sequence group 45 of the primers immobilized in the detected spots are extracted, and ordered so as to overlap with each other while being shifted at the head and tail of the sequences by every single base, so as to obtain an ordered sequence group 47. A base sequence 49 of the template DNA fragment having an unknown base sequence 43 can be determined by reading the head bases of the individual primers according to the order shown by the ordered sequence group 47, and by reading all bases as for the last primer.

It is necessary to prepare 4096 species of primers for 6-mer primers, and 16384 species of primers for 7-mer primers. These primers are applicable to search for relatively small molecules as long as 20 mer to 50 mer, such as funcionally-unknown (nc) RNA and micro (mi) RNA, and to analysis a gene sequence.

It is necessary to prepare 65536 species of primers for 8-mer primers, and 262144 and 1048576 species of primers for 9-mer and 10-mer primers, respectively. These primers are applicable to general gene sequencing.

(Gene Expression Profiling)

Figure 8:
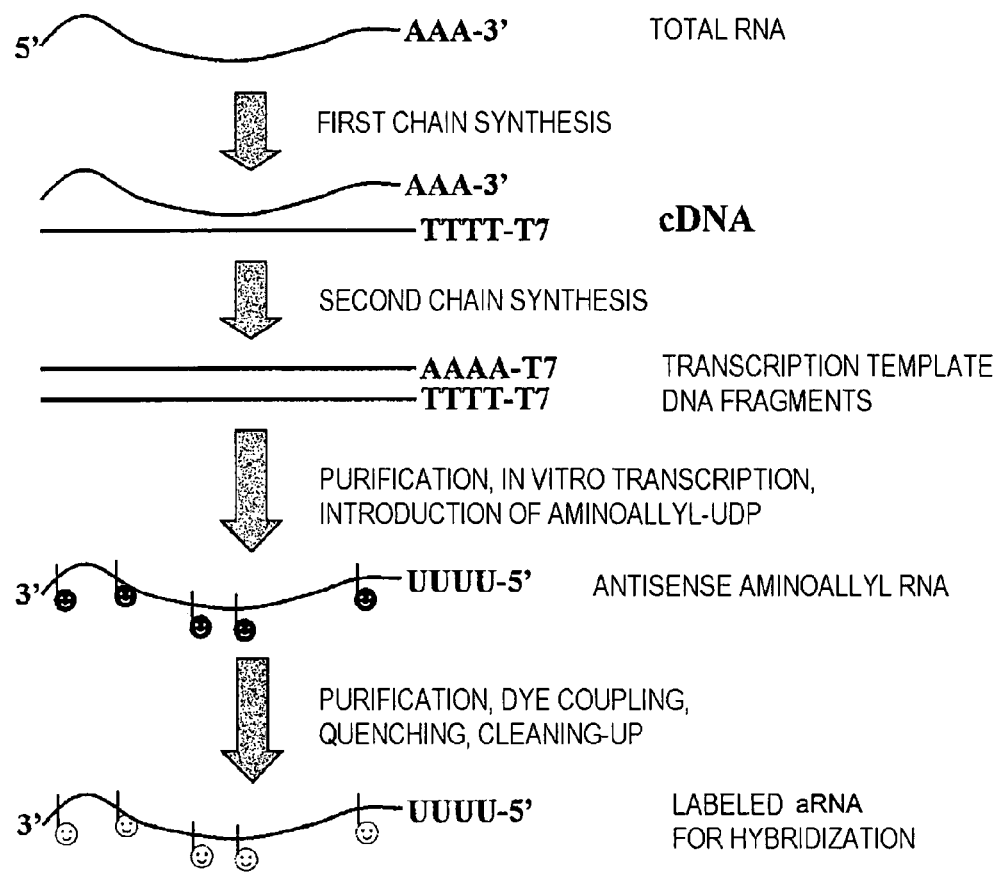
FIG. 8 is a drawing showing an example of conventional gene expression profiling.
Figure 9:
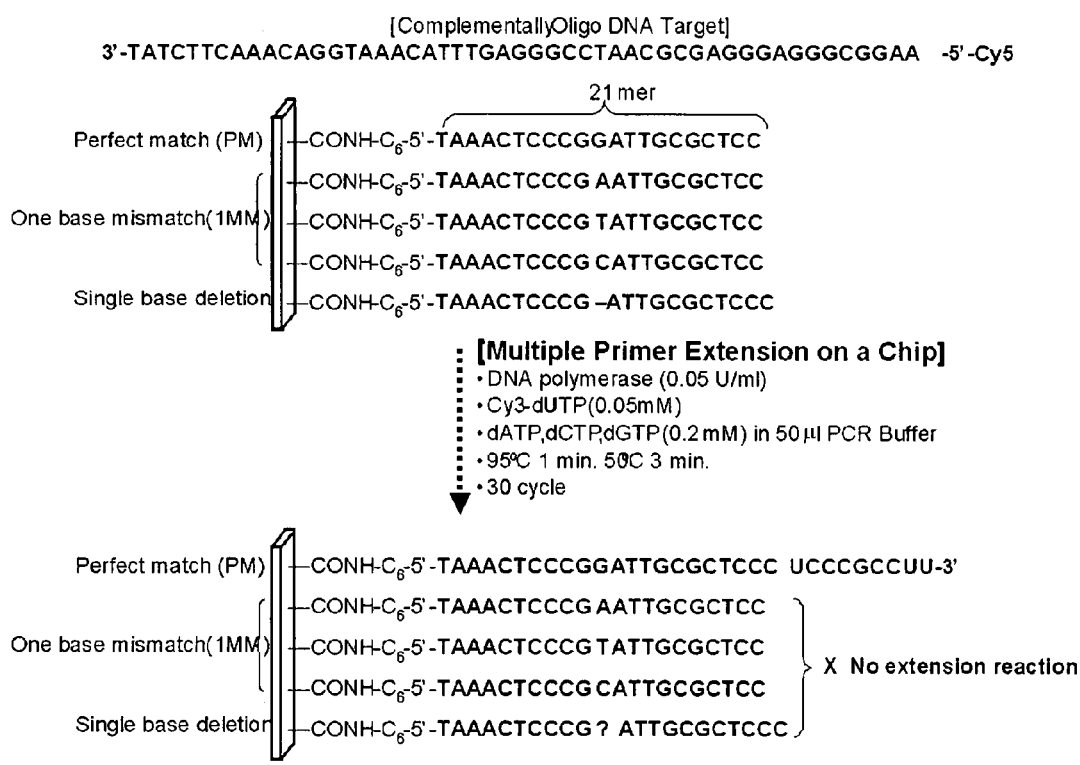
FIG. 9 is a drawing showing another exemplary application of the second embodiment (the sequences from top to bottom are SEQ ID NO:1, SEQ ID NO:9, SEQ ID NO:10, SEQ ID NO:11, SEQ ID NO:12, SEQ ID NO:13, SEQ ID NO:14, SEQ ID NO:10, SEQ ID NO:11, SEQ ID NO:12, and SEQ ID NO:13)

FIG. 8 shows conventional methods of preparing a sample introduced a label as a sample for gene expression profiling and of carrying out the expression profiling.

A total RNA is extracted from an biological tissue corresponded to the purpose. From the total RNA, a cDNA is synthesized (first chain synthesis) based on a reaction using a reverse transcriptase. In the reaction using the reverse transcriptase, a mixture containing a predetermined ratio of dNTP and aminoallyl dUTP is added, to thereby synthesize the cDNA having aminoallyl dUTP incorporated therein.

When only a small amount of total RNA was obtained from the tissue, the cDNA is synthesized by the reverse transcription reaction, a double-strand cDNA (transcription template DNA fragment) is synthesized (second chain synthesis), and using the product as the template, an RNA polymerase is acted thereon so as to amplify an RNA having an antisense chain (aRNA). In the process of RNA amplification, the aRNA having aminoallyl dUTP incorporated therein can be synthesized, by adding a mixture containing a predetermined ratio of dNTP and aminoallyl dUTP.

Next, the cDNA or the antisense aminoallyl RNA (aRNA) is precipitated with ethanol, and is then dissolved into a 0.2 M sodium carbonate buffer ($NaHCO_3$—$Na_2CO_3$ (pH9.0)). A fluorescent dye (Cy3 or Cy5) preliminarily dissolved into DMSO is added, and is allowed to couple with aminoallyl dUTP preliminarily incorporated into the cDNA or the aRNA according to general procedures, to thereby label the cDNA or the aRNA with fluorescence. Unbound portion of the fluorescent dye is removed by general purification procedures through a gel filtration column or a filter, and the aRNA is further added with a fragmentation buffer (having final concentrations of 0.04 M Tris(hydroxymethyl)aminomethane Acetate (pH8.1), 0.1 M potassium acetate, 0.03 M magnesium acetate), allowed to react at 95° C. for 15 minutes, and then quickly quenched with crushed ice, to thereby fragmentate the aRNA. After confirming the fragmentation by a method such as gel electrophoresis, the product is purified and concentrated by gel filtration.

Next, thus-prepared cDNA or aRNA is hybridized with the primers in the microarray. The cDNA or the aRNA is appropriately mixed with a hybridization buffer (final concentration of 5×SSC, 0.5 (v/v) % SDS, 4×Denhardt's solution) and formamide, and hybridized overnight with the DNA microarray at 45° C. to 60° C. After the hybridization, the microarray is washed using a 2×SSC-0.1 (v/v) % SDS solution, a 2×SSC solution, and a 1×SSC solution, respectively for 5 minutes, images are scanned using a fluorescent image reader (for example, CRBIO(r) IIe; from Hitachi Software Engineering, Co., Ltd.), and signal intensities are quantified using an analytical software (for example, DNASIS(r)Array; from Hitachi Software Engineering, Co., Ltd.). Although FIG. 8 shows an exemplary case of aRNA synthesis, cDNA may directly be analyzed if a sufficient quantity of cDNA is available in the middle of the process.

This method, however, needs complicated pretreatment processes, and consequently needs a large number of conditions to be set, such as needing selection of conditions for the individual samples, so that it takes at least 5 days to one week to complete the whole processes, raising a disadvantage in terms of rapid genetic inspection.

Therefore in this embodiment, the DNA fragments having the base sequences corresponded to the characteristic sequence of a gene to be analyzed are used as the primers, and each primer is preliminary immobilized on the surface of the substrate according to the similar method to S10 in FIG. 1 in a single spot on the microarray. The first chain synthesis is then carried out by allowing the total RNA to react with a reverse transcriptase so as to obtain the cDNA, and by using the cDNA (or the aRNA obtained by amplification if the occasions demand) obtained by the first chain synthesis as the template DNA fragments, and the elongation reaction is allowed to proceed on the primer side on the substrate by actions of a DNA polymerase or a DNA ligase, and thereby an expressed gene can be identified.

As described in the above, it is also made possible to directly proceed the elongation reaction on the primer side on the substrate, by hybridizing the primers having predetermined sequences and provided on the substrate, using the total RNA as the templates, under action of a reverse transcriptase, and thereby an expressed gene can be identified.

In other words, whether a probe having a base sequence complementary to a characteristic sequence owned by a known gene can be found or not, in the template DNA fragments obtained from the total RNA derived from a specific cell.

Referring now to the case where cDNA with respect to the total RNA is used as the template DNA fragments, the above-described individual primers are immobilized to the respective spots of the microarray in step S10. In this process, the sequences of the primers immobilized to the detected spots are memorized. In step S20, a sample is introduced while using the cDNA synthesized from a predetermined total RNA obtained as described in the above as the template DNA fragments, thermal unfolding is carried out in step S30, and annealed in step S40. In step S50, the elongation reaction proceeds only on the primers existing in a form of double strand having the template DNA chain fragments annealed therewith.

As described in the above, by preliminarily incorporating the labeled nucleotide monomers into the sample to be introduced in step S20, the DNA fragments obtained from the primers by the elongation reaction are labeled, and the spots containing the fluorescent DNA fragments remained on the substrate after the washing in step S55 can be detected, wherein the sequences of the primers immobilized to the detected spots can be known, because the sequences of the primers immobilized to the individual arrays are memorized. In this way, the base sequences of the primers causing thereon the elongation reaction can be known, and it is therefore made possible to know from which gene the total RNA was expressed and obtained, that is, it is made possible to carry out gene expression profiling.

According to this method, the gene expression profiling analysis can be carried out only by simple operations, excluding most part of labor- and time-consuming sample preparation having been necessary in the general analyses, but using, as the template DNA fragments, cDNA obtained as a reverse-transcription product from genomic DNA or total RNA.

Applications other than those described in the above include:

application to basic tool for gene analysis such as microsatellite analysis, chromosomal abnormality analysis (CGH: Comparative Genomic Hybridization), search for functionally-unknown (nc) RNA;

application to application-specific custom chips using these tools, such as organ- and disease-specific gene expression analyzing chip, mutagenicity test kit (environmental hormone), genetically-modified food inspection kit, mitochondrial gene sequencing kit, analytical kit for paternity test/criminal investigation, congenital disease analyzing kit, chromosomal/genetic abnormality analyzing kit, genetic diagnosis (preimplantation/prenatal) kit, drug-response-related gene polymorphism analyzing kit, lipid-metabolism-related gene polymorphism analyzing kit, and otological/opthalmological field gene polymorphism analyzing kit;

application to diagnostic/clinical custom chips such as cancer prognostic prediction chip, drug development (clinical/drug discovery) chip, and healthy food development chip;

application to microbial identification and inspection kit such as used in drug/food manufacturing processes including for microbial limit test, and microbial inspection of food and drinking water; and clinical inspection in dental field including detection of dental caries/periodontitis-related bacteria and detection of opportunistic infection bacteria; and environmental inspection including environmental inspection for food factory/kitchen facility and water inspection for drinking water/public bath and well water; and health and hygiene field including prevention of infectious disease/food poisoning and health management of company employee; general microbial identification also related to resistant bacteria; and clinical inspection of hepatitis virus, Helicobacterpyroli, hepatitis chlamydia, AIDS virus, SARS virus, West Nile virus, norovirus (food poisoning ascribable to raw oyster), influenza virus, fungus/mold, or the like.

EXAMPLES

Experiment 1

According to the techniques described below, the primers were immobilized onto the surface of each substrate of the plastic and glass substrates corresponded to this embodiment, and the aldehyde substrate corresponded to conventional substrates, the DNA chain elongation reaction was allowed to proceed on the individual substrates, and the DNA chain elongation reaction on the primers was detected.

(Manufacture of Plastic Substrates)

Using a saturated cyclic polyolefin resin (hydrogenated ring-opening product of 5-methyl-2-norbornene, MFR (melt flow rate): 21 g/10 min, ratio of hydrogenation: substantially 100%, thermal deformation temperature 123° C.), slide-glass-formed substrates were obtained by injection molding. The substrates were dipped into a 0.5 wt % ethanol solution of 2-methacryloyloxyethylphosphoryl choline-butyl methacrylate-p-nitrophenyl-oxycarbonyl polyethylene glycol methacrylate (NPMA) copolymer (containing the individual groups in a molar ratio of 25:74:1), so as to introduce a polymer substance having phosphoryl choline groups and activated ester groups onto the surface of the substrates, to thereby obtain plastic substrates.

(Manufacture of Glass Substrates)

General glass substrates were dipped into a 0.5 wt % ethanol solution of 2-methacryloyloxyethylphosphoryl choline-butyl methacrylate-p-nitrophenyl-oxycarbonyl polyethylene glycol methacrylate (NPMA) copolymer (containing the individual groups in a molar ratio of 25:74:1), so as to introduce a polymer substance having phosphoryl choline groups and activated ester groups onto the surface of the substrates, to thereby obtain glass substrates.

(Manufacture of Aldehyde Substrates)

Using a saturated cyclic polyolefin resin (hydrogenated ring-opening product of 5-methyl-2-norbornene, MFR (melt flow rate): 21 g/10 min, ratio of hydrogenation: substantially 100%, thermal deformation temperature 123° C.), slide-glass-formed substrates were obtained by injection molding. The mold products were then subjected to low-temperature plasma treatment, so as to hydrophilize the surface. Next, γ-aminopropyl triethoxysilane as aminoalkylsilane was dissolved into methanol in a concentration of 5% so as to prepare an amino group introducing solution, the substrates were dipped in the solution for 2 hours, taken out from the solution, dipped in a ultrapure water, allowed to stand, taken out therefrom, and dried. Glutaraldehyde was dissolved into PBS PBS (−) in a concentration of 2% so as to prepare a glutaraldehyde solution, the aminoalkylsilane-treated substrates were dipped in the glutaraldehyde solution, allowed to stand for 4 hours, taken out, immersed in a ultrapure water, and then washed and dried. Aldehyde substrates having aldehyde groups on the surface thereof were obtained.

(Immobilization of Primers)

An oligo DNA (20 bases) having an amino group on the 5'-terminal was dissolved into a 0.25 M carbonate buffer (pH9.0) to thereby prepare a 10-μM oligo DNA solution. The solution was spotted using a spotter (Marks-I from Hitachi Software Engineering, Co., Ltd.) with a 100-μm-diameter crosscut pin, respectively onto the surfaces of the plastic substrates, the glass substrates, and the aldehyde substrates. The individual substrates spotted with the oligo DNA were kept overnight in a closed container (10 cm×15 cm×3 cm) moistened inside thereof with 200 μl of a 0.25 M phosphate buffer (pH8.5), so as to immobilize the oligo DNA (primers).

(DNA Chain Elongation Reaction)

By using predetermined 50-mer DNA fragments preliminarily labeled at the 5'-terminal thereof with Cy5 were as the template DNA fragments to be introduced in step S20 of FIG. 6, a reaction system was prepared while adjusting the concentration of the template DNA fragments to 100 μM. As the enzyme system for the DNA chain elongation, a DNA polymerase (Ex Taq from Takara Bio Inc.) was used.

Next, the thermal unfolding in step S30 of FIG. 6, the annealing in step S40 and the elongation reaction in step S50 were carried out at 95° C. for 5 minutes (unfolding), 95° C. for 1 minute (unfolding), 50° C. for 3 minutes (annealing), and 95° C. for 1 minute (unfolding), respectively.

Table 1 below shows results of measurement of fluorescent intensity ascribable to Cy3-dUTP in the detection of the DNA chain elongation reaction, while preliminarily incorporating Cy3-dUTP into the sample.

TABLE 1

| NUMBER OF BASES IN PROBES | FLUORESCENCE INTENSITY(MPEC ELONGATION REACTION) | | |
|---|---|---|---|
| | PLASTIC | GLASS | ALDEHYDE SUBSTRATE |
| 20 | 6281 | 3383 | 1725 |
| 25 | 3602 | 2412 | 0 |

The DNA chain elongation on the substrates was detected on the plastic substrates and glass substrates corresponded to this embodiment, whereas the DNA chain elongation was supposed as being not detected on the aldehyde substrates corresponded to the conventional substrates.

Experiment 2

Using the plastic substrates on which the DNA chain elongation reaction was detected in Experiment 1, DNA chain elongation of 20-mer, 25-mer and 30-mer probes was respectively carried out based on the MPEC method in 1 cycle, 5 cycles, 10 cycles and 20 cycles, so as to amplify the DNA chains, and fluorescent intensity was measured when every set of cycles is completed.

The thermal unfolding in step S30 of FIG. 1, the annealing in step S40, the elongation reaction in step S50, and the thermal unfolding step S60 were carried out at 95° C. for 5 minutes (unfolding; only for the first time), 95° C. for 1 minute (unfolding), 50° C. for 3 minute (annealing) and 95° C. for 1 minute (unfolding), respectively.

Results are shown in Table 2 below.

TABLE 2

| NUMBER OF BASES IN PROBES | FLUORESCENCE INTENSITY (AFTER ELONGATION REACTION BY THE MPEC METHOD) NUMBER OF MPEC CYCLES | | | |
|---|---|---|---|---|
| | 1 | 5 | 10 | 20 |
| 20mer | 6487 | 14012 | 35502 | 45668 |
| 25mer | 3808 | 5348 | 15287 | 35469 |
| 30mer | 2766 | 4340 | 9656 | 27939 |

On the plastic substrates treated on the surface thereof with a predetermined polymer substance, the DNA chain amplification was detected for any length of probes.

Experiment 3

For the purpose of SNS typing having the 21st base C from the 5' position of SEQ ID NO:1 labeled on the 3'-terminal thereof with Cy5 (5'-Cy5-AAGGCGGGAGGGAGCG-CAATCCGGGAGTTTACAAATGGACAAACTTCTAT-3') as a mutant site, total 5 species of probes (21 mer) were designed, and immobilized on the plastic substrates. Using these microarrays, SNP typing (elongation reaction) is carried out based on the MPEC (multiple primer extension on a chip) reaction.

The SNP typing is carried out under the presence of a DNA polymerase (0.05 U/ml), Cy3-dUTP (0.05 mM), and dATP, dCTP and dGTP (respectively in a concentration of 0.2 mM) in 50 μl of a PCR buffer, under a temperature cycle of 95° C. (1 minute) and 50° C. (3 minutes).

As a result of the elongation reaction, only completely-matched sequence probes having a sequence complementary with the target, which is the 50-mer DNA fragments described in the above, are elongated, and consequently emit fluorescence.

Experiment 4

The MPEC reaction described in Example 1 will be applied to detection of p53 cancer suppressor gene.

High incidence of abnormalities in the p53 gene have been found in colon cancer and lung cancer, and abnormality in the p53 gene (single base polymorphism: SNP) will reduce efficacy of anticancer agents, fail in inducing apotosis of cancer cells, and thereby allows the cancer cells to proliferate.

The SNP typing (elongation reaction) using normal p53 gene and p53 gene of cancer cell will be carried out. Mutation on the 993-rd position and the 1069-th position of the p53 gene have publicly been known, and probes having on the 3'-terminals thereof the bases at these positions, and having an almost constant Tm value are designed, and immobilized on the plastic substrates. Thus designed 16 species of probes 5'-ATGGGCGGCATGAACN-3'(SEQ ID NO:2), 5'-TGAG-GATGGGCCTCCN-3' (SEQ ID NO:3), 5'-GGAA-CAGCTTTGAGGTGCN-3' (SEQ ID NO:4) and 5'-CCAG-GACAGGCACAAACAN-3' (SEQ ID NO:5) (N=A, G, C, T) are used for the SNP typing based on the MPEC reaction.

Experiment 5

A simulation experiment for determining and analyzing a base sequence based on the SBH method will be carried out.

Figure 10:
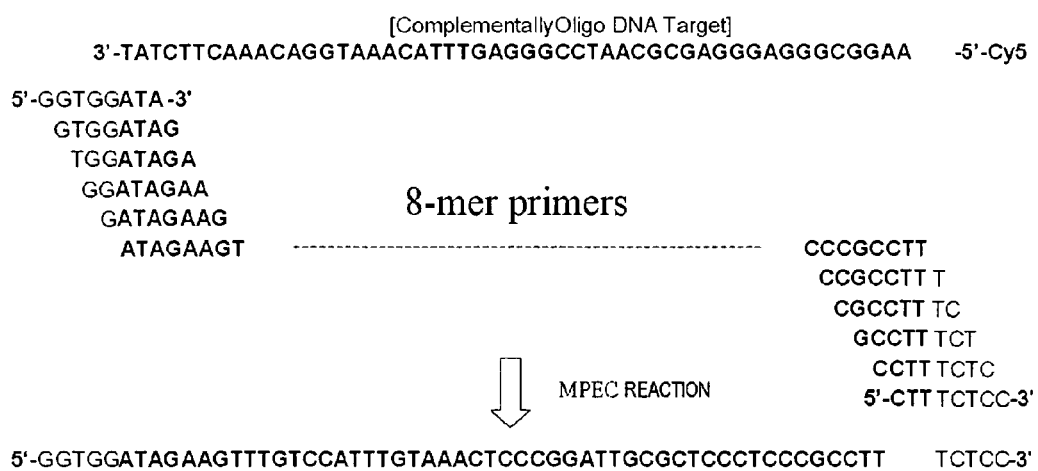
FIG. 10 is a drawing showing still another exemplary application of the second embodiment (the 50-mer sequence is SEQ ID NO:1 and the 60-mer sequence is SEQ ID NO:15).

As shown in FIG. 10, in order to make it possible to determine a base sequence of a 50-mer target labeled on the 5'-terminal thereof with Cy5, SBH based on the MPEC reaction is carried out using microarrays immobilized on the plastic substrates thereof, 8-mer probes (50 in total) having base sequences shifted by every single base in the direction of the 3'-terminal. Fifty species of probes, respectively having one mismatched base on the 3'-terminals thereof were also added and immobilized onto the substrates. By using the SBH simulation array, base sequencing is carried out.

The invention claimed is:

1. A method of elongating DNA chains comprising:
immobilizing primers for DNA elongation onto a substrate having on the surface thereof a copolymer of a first monomer having a 2-methacryloyloxyethyl-phosphoryl choline (MPC) group, a second monomer having p-nitrophenyloxycarbonyl polyethylene glycol methacrylate (NPMA) group, and a third monomer having a butyl methacrylate (BMA) group, wherein said substrate is obtained by which a base material composed of saturated cyclic polyolefins is coated by or dipped into a liquid containing said copolymer, and then dried, wherein the primer has an amino group, and the primer is immobilized onto the surface of the substrate via a covalent bond formed by the reaction of the amino group of the primer with the p-nitrophenyloxycarbonyl group contained in the NPMA with leaving of the p-nitrophenyloxy group of the p-nitrophenyloxycarbonyl group;

introducing a sample containing template DNA fragments or template RNA fragments having desired sequences, an enzyme system for DNA chain elongation and nucleotide monomers into the substrate to thereby form a reaction system containing the substrate and the sample, heating said reaction system up to a temperature causing thermal unfolding of the DNA chains (referred to as "thermal unfolding temperature", hereinafter);

cooling said reaction system down to a temperature for annealing (referred to as "annealing temperature", hereinafter); and allowing elongation reaction of the DNA chains to proceed in said reaction system.

2. The method of elongating DNA chains as claimed in claim 1, having no washing process involved between the annealing and the elongation reaction of the DNA chains, in said reaction system.

3. The method of elongating DNA chains as claimed in claim 1,
wherein said enzyme system for DNA chain elongation is either one of DNA polymerase and DNA ligase, when said templates are DNA fragments.

4. The method of elongating DNA chains as claimed in claim 1,
wherein said enzyme system for DNA chain elongation is either reverse transcriptase, or a combination of DNA ligase and reverse transcriptase, when said templates are RNA fragments.

5. The method of elongating DNA chains as claimed in claim 1,
wherein said DNA chain elongation reaction is allowed to proceed, while gradually elevating the temperature of said reaction system from said annealing temperature to said thermal unfolding temperature.

6. The method of elongating DNA chains as claimed in claim 1,
wherein said DNA chain elongation reaction is allowed to proceed, while changing the temperature of said reaction system to a predetermined temperature between said annealing temperature and said thermal unfolding temperature.

7. The method of elongating DNA chains as claimed in claim 1,
wherein each of said primers is a DNA fragment in which one base of a base sequence containing a characteristic sequence of a predetermined target gene is replaced with another base.

8. The method of elongating DNA chains as claimed in claim 1,
wherein each of said primers is composed of a predetermined number of base sequences, and is a DNA fragment having its own sequence out of complete sets.

9. The method of elongating DNA chains as claimed in claim 1,
wherein each of said template DNA fragments is a cDNA fragment obtained by treating a predetermined RNA with a reverse transcriptase.

10. The method of elongating DNA chains as claimed in claim 1,
wherein at least one species of said nucleotide monomers contained in the sample introduced into said reaction system is labeled.

11. A method of amplifying DNA chains comprising:
immobilizing primers for DNA elongation onto a substrate having on the surface thereof a copolymer of a first monomer having a 2-methacryloyloxyethyl-phosphoryl choline (MPC) group, a second monomer having p-nitrophenyloxycarbonyl polyethylene glycol methacrylate (NPMA) group, and a third monomer having a butyl methacrylate (BMA) group, wherein said substrate is obtained by which a base material composed of saturated cyclic polyolefins is coated by or dipped into a liquid containing said copolymer, and then dried, wherein the primer has an amino group, and the primer is immobilized onto the surface of the substrate via a covalent bond formed by the reaction of the amino group of the primer with the p-nitrophenyloxycarbonyl group contained in the NPMA with leaving of the p-nitrophenyloxy group of the p-nitrophenyloxycarbonyl group;
introducing a sample containing template DNA fragments or template RNA fragments having desired sequences, an enzyme system for DNA chain elongation and nucleotide monomers into the substrate to thereby form a reaction system containing the substrate and the sample,
heating said reaction system up to a temperature causing thermal unfolding of the DNA chains (referred to as "thermal unfolding temperature", hereinafter);
cooling said reaction system down to a temperature for annealing (referred to as "annealing temperature", hereinafter);
allowing elongation reaction of the DNA chains to proceed in said reaction system;
allowing thermal unfolding of the DNA chains to proceed; and
allowing annealing, elongation reaction and thermal unfolding to proceed if necessary.

12. The method of amplifying DNA chains as claimed in claim 11,
having no washing process involved between the annealing and the elongation reaction of the DNA chains, in said reaction system.

13. The method of amplifying DNA chains as claimed in claim 11,
wherein said enzyme system for DNA chain elongation is either one of DNA polymerase and DNA ligase, when said templates are DNA fragments.

14. The method of amplifying DNA chains as claimed in claim 11,
wherein said enzyme system for DNA chain elongation is either reverse transcriptase, or a combination of DNA ligase and reverse transcriptase, when said templates are RNA fragments.

15. A microarray for DNA chain elongation comprising:
a substrate having on the surface thereof a copolymer of a first monomer having a 2-methacryloyloxyethyl-phosphoryl choline (MPC) group, a second monomer having p-nitrophenyloxycarbonyl polyethylene glycol methacrylate (NPMA) group, and a third monomer having a butyl methacrylate (BMA) group, wherein said substrate is obtained by which a base material composed of saturated cyclic polyolefins is coated by or dipped into a liquid containing said copolymer, and then dried; and
a primer for DNA elongation immobilized onto the surface of said substrate, wherein the primer has an amino group, and the primer is immobilized onto the surface of the substrate via a covalent bond formed by the reaction of the amino group of the primer with the p-nitrophenyloxycarbonyl group contained in the NPMA with leaving of the p-nitrophenyloxy group of the p-nitrophenyloxycarbonyl group.

16. The microarray for DNA chain elongation as claimed in claim 15,
wherein said group derived from phosphoester contained in the first unit of said substrate is any one of phosphoryl choline group, phosphoryl ethanolamine group, phosphoryl serine group, phosphoryl inositol group, phosphoryl glycerol group, and phosphatidyl phosphoryl glycerol group.

17. The microarray for DNA chain elongation as claimed in claim 15,
wherein said substrate is composed of a plastic material.

18. The microarray for DNA chain elongation as claimed in claim 15,
wherein each of said primers is composed of a base sequence having 5 to 50 bases.

19. The microarray for DNA chain elongation as claimed in claim 15,
wherein each of said primers is immobilized to the surface of said substrate through a covalent bond formed at the site of a carboxylic acid-derived group of said substrate.

20. The microarray for DNA chain elongation as claimed in claim 15,
wherein said polymer substance has a third unit containing a butyl methacrylate group.

21. The microarray for DNA chain elongation as claimed in claim 15,
wherein said substrate contains, in addition to said polymer substance, a second polymer substance which contains a first unit having a group derived from a phosphoester composing the hydrophilic section of a phospholipid, and a third unit which contains a butyl methacrylate group.

22. The microarray for DNA chain elongation as claimed in claim 15,
wherein said substrate has a plurality of spots within a certain section, each of said spots having the primers immobilized thereto.

\* \* \* \* \*

UNITED STATES PATENT AND TRADEMARK OFFICE
CERTIFICATE OF CORRECTION

PATENT NO. : 8,765,417 B2  
APPLICATION NO. : 11/792512  
DATED : July 1, 2014  
INVENTOR(S) : Kenji Kinoshita Page 1 of 1

It is certified that error appears in the above-identified patent and that said Letters Patent is hereby corrected as shown below:

Title page, item (73) "Assignees", add the following Assignee:

-- Kenji Kinoshita, Hyogo (JP) --.

Signed and Sealed this  
Second Day of December, 2014

Michelle K. Lee  
*Deputy Director of the United States Patent and Trademark Office*